(12) United States Patent
Numata et al.

(10) Patent No.: US 6,647,085 B2
(45) Date of Patent: Nov. 11, 2003

(54) DATA PROCESSING METHOD AND DATA PROCESSING APPARATUS

(76) Inventors: Shouhei Numata, c/o Hitachi, Ltd., Intellectual Property Group New Marunouchi Bldg. 5-1, Marunouchi 1-chome, Chiyoda-ku, Tokyo 100-8220 (JP); Tarou Takagi, c/o Hitachi, Ltd., Intellectual Property Group New Marunouchi Bldg. 5-1, Marunouchi 1-chome, Chiyoda-ku, Tokyo 100-8220 (JP)

( * ) Notice: Subject to any disclaimer, the term of this patent is extended or adjusted under 35 U.S.C. 154(b) by 0 days.

(21) Appl. No.: 10/194,254

(22) Filed: Jul. 15, 2002

(65) Prior Publication Data

US 2003/0026389 A1 Feb. 6, 2003

Related U.S. Application Data

(63) Continuation of application No. 10/086,714, filed on Mar. 4, 2002.

(30) Foreign Application Priority Data

Aug. 2, 2001 (JP) ........................................ 2001-234387

(51) Int. Cl.[7] .................................................. A61B 6/03
(52) U.S. Cl. .......................................... 378/4; 378/901
(58) Field of Search ............................ 378/4, 8, 15, 19, 378/901

(56) References Cited

FOREIGN PATENT DOCUMENTS

| JP | 1202788 A | * | 8/1989 |
|----|-----------|---|--------|
| JP | 6-202612  |   | 7/1994 |
| JP | 6-251078  |   | 9/1994 |
| JP | 7-182366  |   | 7/1995 |
| JP | 8-287091  |   | 11/1996 |
| JP | 2001-204725 | | 7/2001 |

OTHER PUBLICATIONS

Nelson et al., "Temperature, Pressure, and Infrared Image Survey of an Axisymmetic Heated Exhaust Plume", Ames Research Center, Moffett Field, CA, Feb. 1996 (abstract).*

Y. Shuudou, "Three–Dimensional Image Processing in Medical Science", Corona Publishing Co., Ltd., 1995.

* cited by examiner

*Primary Examiner*—David V. Bruce
(74) *Attorney, Agent, or Firm*—Mattingly, Stanger & Malur, P.C.

(57) ABSTRACT

A data processing apparatus comprising a display device for displaying the data; the first recording device for recording the large volume bit map data; the second recording device recording an index data formed as a two-dimensional image obtained by rendering the large volume bit map data; the first data processing device for reading the large volume bit map data from the first recording device and applying the image processing to the-large volume bit map data; the second data processing device for reading the large volume bit map data from the first recording device, forming the two-dimensional image data by rendering the large volume bit map data and transferring the image data to the display device; the third data processing device for transmitting the index data to the display device; and the input device for sending the instructions to the first, second and third data processing devices.

4 Claims, 16 Drawing Sheets

DATA PROCESSING METHOD AND DATA PROCESSING APPARATUS

This is a continuation application of U.S. Ser. No. 10/086,714, filed Mar. 4, 2002.

BACKGROUND OF THE INVENTION

The present invention relates to the data processing method and the data processing apparatus thereof.

In case of applying X-ray Computed Tomography (hereinafter referred to as X-ray CT) to non-contact internal dimensional measurement, various kinds of three-dimensional image processing are applied to the three-dimensional bit map data obtained by stacking multi-layered tomographic images defined as two-dimensional bit map data. This technology is used in the medical field, and described in the publication (for example, Three-dimensional image processing in Medical Science by Yasuzo Shuudou, Corona Publishing Co., 1995).

In many cases, for various kinds of data processing for three-dimensional image processing, the following procedures are used. That is, the user supplies commands to the program and the program in response to those commands processes the data (this is called interactive).

In this interactive process, it is required to minimize the user's additional operations due to his or her erroneous operation. For this reason, many programs provides an undo (data and/or operation recovery) function. This function means that the data before processing is stored temporarily, and the data after processing is replaced by the data before processing when the undo command is issued. The user who has noticed his or her erroneous operation can cancel his or her latest operation by inputting the undo command and restart his or her operation from this point. If several sets of data before processing could be stored temporarily, the user can cancel several latest operations backward and restart the operation at any point.

In association with the function described above, Japanese Patent Laid-Open Number 6-251078 (1995) discloses an information processing apparatus in which scale-down image data corresponding to the image data represented as bit map data are arranged and the list of scale-down image data are shown and made selected. Japanese Patent Laid-Open Number 6-202612 (1995) discloses a graphic editor apparatus which provides a display part having a display area for the image edition allowing the user to edit the image and a target object image display area for displaying plural screens of the images in process of edition work.

The prior art described above does not consider the processing of large amount of three-dimensional bit map data over several hundreds megabyte obtained by the high resolution X-ray CT (in this specification, the data having the volume between 100 megabyte and 1 Peta byte is called large amount of data). In many cases, the volume of data is limited below 1P (1 Peta byte) because the technical difficulty occurs in dealing large amount of data.

The volume of the three-dimensional bit map data is proportional to the cubic of the long dimension of the image. A direct application of the apparatus disclosed in Japanese Patent Laid-Open Number 6-251078 (1995) and the conventional method used for three-dimensional bit map operation in the conventional practical field of medical science may arise some problems.

According to the original experiment by the inventors, in case of dealing such large amount of three-dimensional bit map data, it is understood that it takes 10 minutes or longer to display fully the data even by the current computer performance. This is because the image processing called rendering is required to display the three-dimensional bit map data, and it may take an extended time to complete this operation in case that the volume of data is too large. From the user's view, in case of displaying the data in order to confirm the content of the data, such an extended time is required for processing the individual data file in order to browse the content of the individual data.

In case of applying the technology disclosed in Japanese Patent Laid-Open Number 6-251078 (1995) to the three-dimensional bit map data used in the field of medical science, as the time spent in generating the scale-down bit map data from the three-dimensional bit map data (in this case, the volume of data is relatively small) is longer than the time spent for rendering the original three-dimensional bit map data and displaying the resulting image, the time required for confirming the content of the file does not make any significant problem.

In the method for generating the scale-down data of the overall data set later on to be used for search, as disclosed in Japanese Patent Laid-Open Number 6-251078 (1995), there is such a problem that the scale-down operation for the data is required to be done by the user.

In the process of large amount of three-dimensional bit map data, its process itself gives rise to a problem. There may be such a condition that the memory space runs short if the data is stored in the memory every time when the process is repeated. Thus, the number of undo operations (the number of allowable operations to be cancelled) is limited.

In such a method that the rendering operations is performed and the data is displayed every time when the undo command is issued, if the number of undo operations is larger, the fraction of the total waiting time for the user occupied in the overall operation time becomes extremely long because it takes an extended time to be spent for display process.

SUMMARY OF THE INVENTION

An object of the present invention is to provide a data processing method and its processing apparatus enabling to display an preview image rapidly in case of processing large amount of data.

In order to attain the above object, in the present invention, index data are generated by rendering the large amount of bit map data and stored in addition to the three-dimensional bit map data.

It is required to render the large amount of bit map data in order to generate a display image. The rendering process requires an extended period of time. On the contrary, by means that the two-dimensional image resulted from the rendering process is made prepared in advance before accepting the user's command for display and edit, the preview of the content of the data can be displayed rapidly at real-time when the user issues the command interactively.

BRIEF DESCRIPTION OF THE DRAWINGS

FIG. 13 is an example of three-dimensional bit map data format.

DETAILED DESCRIPTION OF THE PREFERRED EMBODIMENTS

Embodiment 1

An embodiment of processing the three dimensional bit map data is described below.

Figure 20:
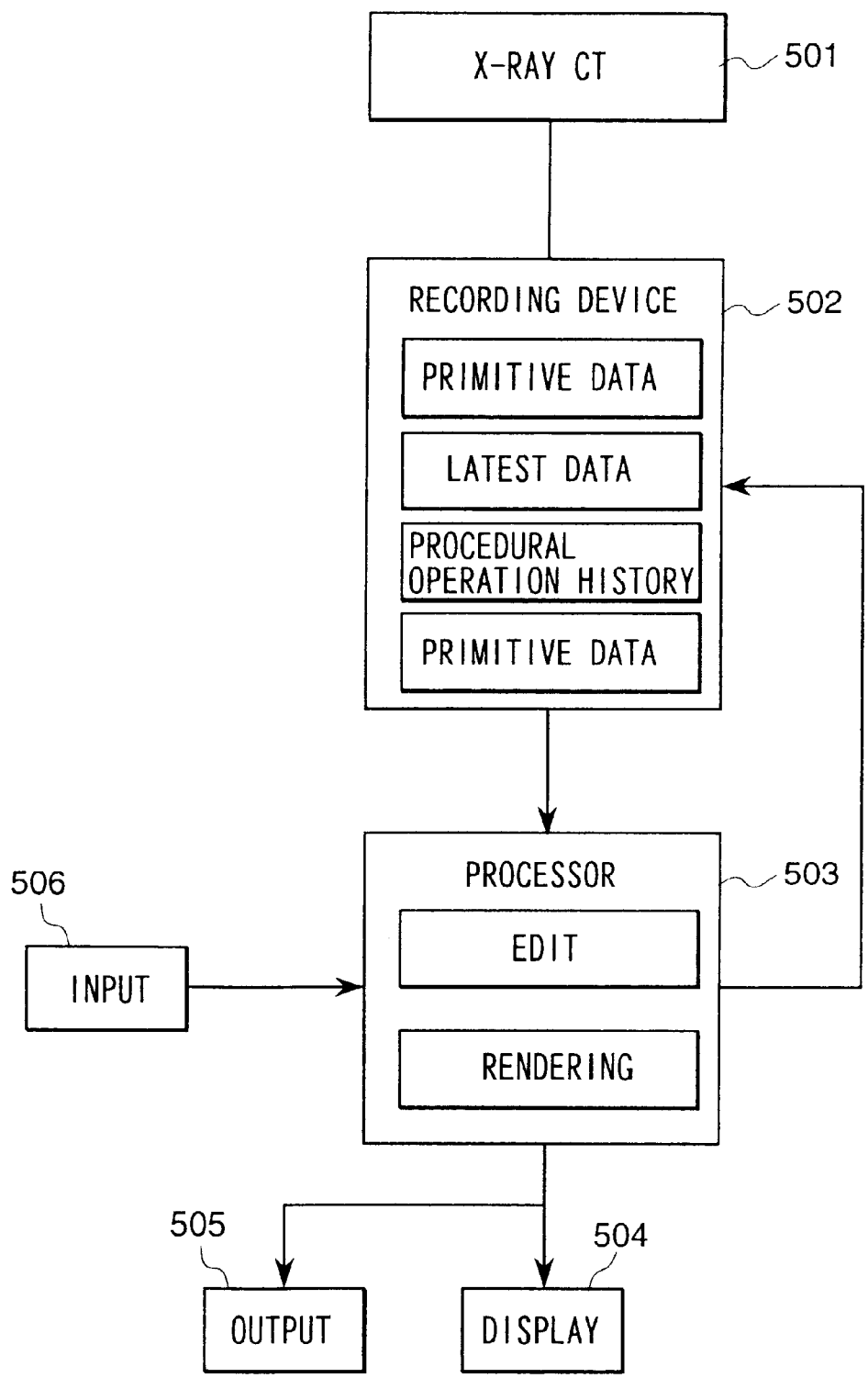
FIG. 20 is a system conceptual diagram.

The outline of the processing apparatus to be used in this embodiment is now described. FIG. 20 shows a conceptual diagram of the processing apparatus. The processing apparatus stores the data taken by the X-ray CT 501 in the storage device 502. The user issues commands to the electronic computer 503 by the input means 506, and specifies various operations. The electronic computer 503 accordingly reads out the necessary data from the memory device 502. The memory device 502 stores the primitive 3DBMD 102, the latest 3D BMD 103, the process history data 105 and the index data 106 to be described later. In response to the commands issued from the input apparatus 506, the electronic computer 503 outputs the data specified by the commands issued by the input apparatus to the output means 505 (printer) and the display device 504 (display). The electronic computer 503 can perform a editing operation for the various data a rendering operation for data (to be describe later). The electronic computer 503 can stores the data into the memory device 502 if required. The concept of the overall processing apparatus is so described as above.

Next, the processing apparatus will be described concretely. At first, the image of the target object is captured by the three-dimensional X-ray CT. The target object in this embodiment is assumed to be a metallic turbine for the automobile turbo engines (not shown). The three-dimensional X-ray CT is formed as such an apparatus that the X-ray is irradiated as a fan beam and the image of the target object is captured by detecting the X-ray transmitted through the target object is detected by the sensors. The captured image is stored in the memory device (formed as a hard disk in this embodiment) as the primitive three-dimensional bit map data (hereinafter, three-dimensional bit map data is referred to as 3DBMD).

Figure 4:
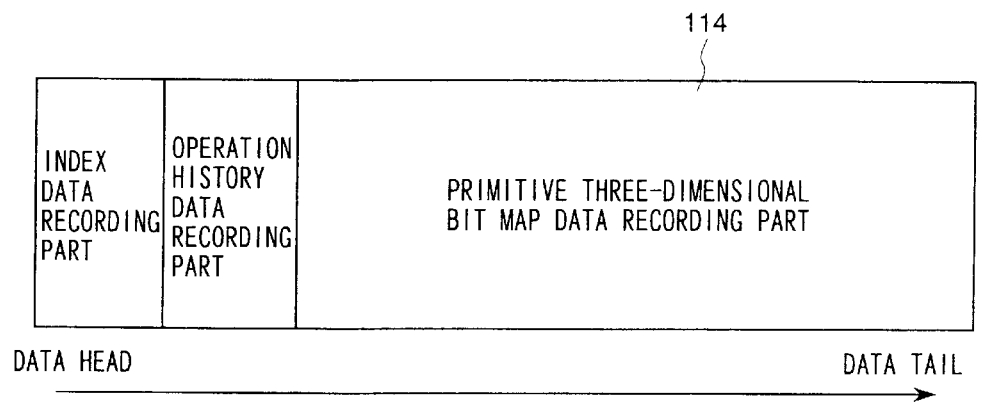
FIG. 4 is an example of three-dimensional bit map data format
Figure 5:
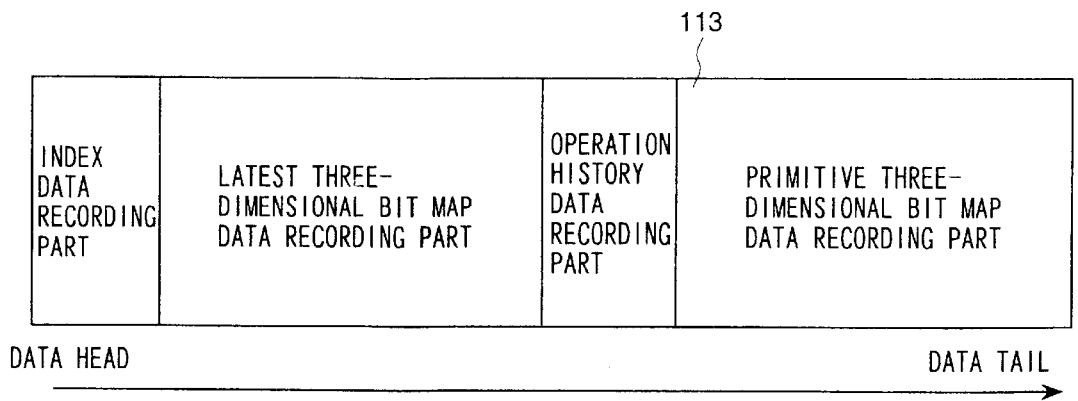
FIG. 5 is an example of three-dimensional bit map data format

Next, the primitive 3DBMD is made converted to the 3DBMD specific to this embodiment. FIG. 4 and FIG. 5 show the formats of the 3DBMD specific to this embodiment.

The header of the 3DBMD 114 with index and procedural operation history shown in FIG. 4 contains the index data recording part and next the procedural operation history data recording part, followed by the recording part for the primitive 3DBMD. The index data represent plural two-dimensional images (or a single image, if allowable) formed by viewing the primitive 3DBMD in a single direction or plural directions. In this embodiment, the data format of the index data is such a format as to be displayed without rendering. In this embodiment, JPEG so-called generally is used for this data format. It is allowed to use GIF so called generally.

The index data is generated by forming the two-dimensional image by viewing the primitive data in a predetermined direction after obtaining the primitive 3DBMD captured by X-ray CT. The formation of the index data is to render the primitive 3DBMD and generate the two-dimensional image. This formation is completed before browsing and processing 3DBMD.

When displaying the index data (two-dimensional image, in this embodiment), the rendering process is not required. The volume of the data is smaller than the volume of the primitive 3DBMD. Thus, the time spent for displaying the index data can be made shorter than the time spent for generating the two-dimensional image from the primitive 3DBMD and displaying the generated image. In addition, by means of generating the index data before hand, the content of the data can be confirmed in a shorter period of time than the two-dimensional data is generated from the 3DBMD every time when the browsing operation is attempted. And furthermore, by means of reading only the index data, it is allowed to refer briefly to the content of the primitive 3DBMD without reading the primitive 3DBMD. For the large volume of 3DBMD, as the volume of its index data is so small, from one per several tens to one per some hundreds of the volume of 3DBMD, the volume of the index data remains unchanged for any case.

In addition, the two-dimensional data obtained by processing the primitive 3DBMD in the process of browsing operations are recorded into the index data.

The procedural operation history data recording part records the history of operations applied to the primitive 3DBMD. In case that the user requires an image to be obtained by processing further the index data corresponding to the state of the processed primitive 3DBMD, the primitive 3DBMD is so processed as to be the state corresponding to the index data, and further processed so as to be the required image.

The primitive 3DBMD with index and procedural operation history 113 shown in FIG. 5 has such a data format that records the primitive 3DBMD concurrently when storing the latest processed 3DBMD. The data format contains a header for the index data and next the latest 3DBMD-recording part followed by the procedural operation history data recording part and the primitive 3DBMD recording part. The index data 106 records the rendered image of the latest 3DBMD and the rendered data obtained in the series of procedures from the primitive 3DBMD to the latest 3DBMD as the index data. The procedural operation history data records a series of procedures applied from the primitive 3DBMD to the latest 3DBMD. This means that the application of the series of procedures recorded in the procedural operation history data to the primitive 3DBMD can generate the latest 3DBMD. According to this data format, the outline of the latest 3DBMD can be confirmed briefly at first by displaying the index data. In case of attempting to regenerate the latest 3DBMD (when undo the past processing applied to the latest 3DBMD), the desired 3DBMD to be obtained by applying the undo operation for the past processing can be generated equivalently by applying the procedural operation history data corresponding to the designated step to the series of past procedures to the primitive 3DBMD by referring to the primitive 3DBMD and the procedural operation history data.

Figure 1:
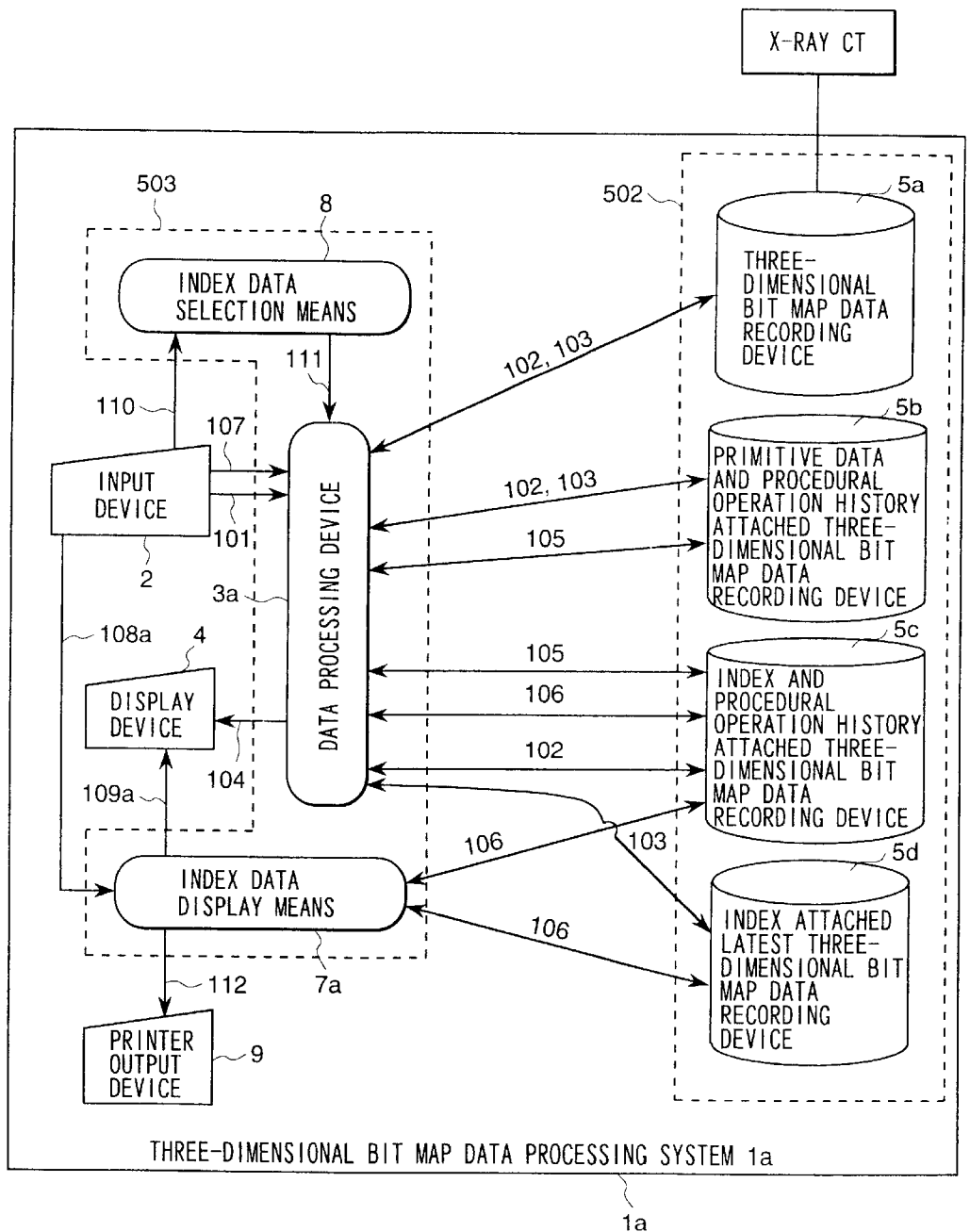
FIG. 1 is a system configuration diagram.

FIG. 1 illustrates a schematic diagram of the 3DBMD processing system 1a using two formats of 3DBMD. This system assumes that the 3DBMD is processed interactively by the user inputting the data processing method (commands) from the input device 2. In this embodiment, the storage device 502 is so configured as to includes individually the 3DBMD recording device 5a, the primitive, index and procedural operation history attached 3DBMD recording device 5b, the index and procedural operation history attached 3DBMD recording device 5c and the index attached the latest 3DBMD 5d, but the storage device 502 may be formed alternatively in another configuration as far as recording those elements of data. The electronic computer 503 is so configured as to include individually the index data selection means 8, the data processing device 3a and the index data display means 7a, each corresponding to their specific tasks, which may be formed as a single computer performing those tasks.

In response to the command input by the user, the input device 2 generates the data processing command 101 and the index data selection command 110. The 3DBMD processing system 1a has a display device 4 for displaying the 3D bit map display image data 104 and the index data display data 109a.

The processing system 1a has the following three recording devices. The 3DBMD recording device 5a records the primitive 3DBMD 102 and the latest 3DBMD. The primitive, index and procedural operation history attached 3DBMD recording device 5b records the primitive, index and procedural operation history attached 3DBMD 113. The index and procedural operation history attached 3DBMD recording device 5c records the index and procedural operation history attached 3DBMD 114. The data processing device 3a can read out the latest 3DBMD 103, the primitive 3DBMD data 102 and the procedural operation history data 105 separately from the primitive, index and procedural operation history attached 3DBMD recording device 5b. The data processing device 3a can read out the index data 106, the procedural operation history data 105 and the primitive 3DBMD 102 separately from the index and procedural operation history attached 3DBMD recording device 5c.

The 3DBMD processing system 1a has the following configuration. The data processing device 3a generates the recording history data 105 and the index data 106 from the primitive 3DBMD 102 and the latest 3DBMD 103. The data processing device 3a also performs various procedures in response to another command. In response to the index data display command 108a, the index data display means 7a generates the index data display data 109a from plural sets of index data 106, and transfers it to the display device 4. In response to the index data selection command 110, the index data selection means 8 generates the reprocessing command 111 and transfer it to the data processing device 3a.

Figure 2:
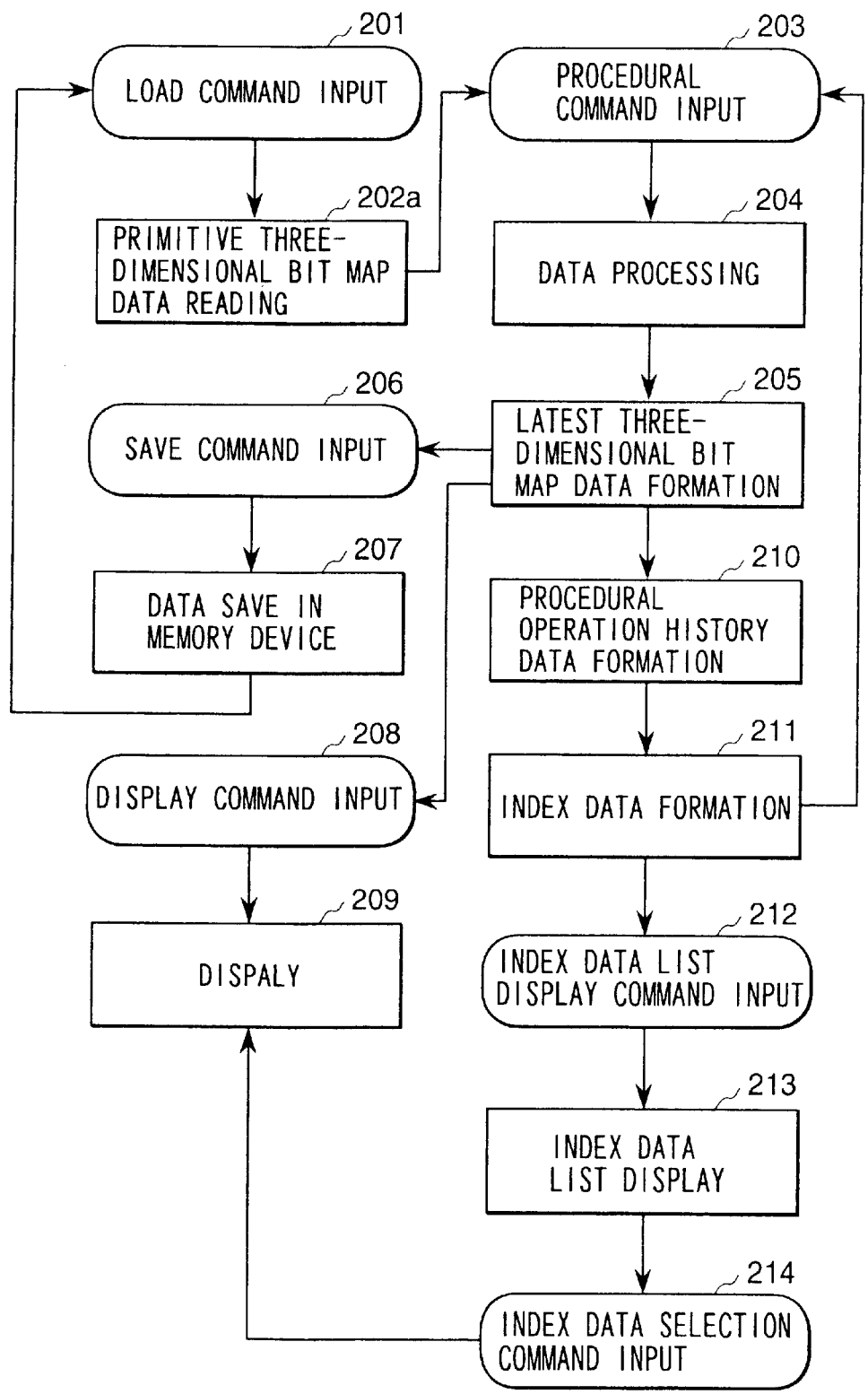
FIG. 2 is a process flowchart.

Next, FIG. 2 illustrates a flowchart for processing the 3DBMD without index data and procedural operation history data in the 3DBMD processing system 1a. This flowchart shows the procedures in which the index data and the procedural operation history data are generated along with processing the 3DBMD in order to speed up the plural sets of procedures (or the procedures in the next phase or later).

The data are exchanged among the individual devices shown in FIG. 1 at the each step of the procedural flow.

At first, the user inputs the load command 201 by using the input device 2. In response to the load command 201, the data processing device 3a reads in the primitive 3DBMD 102 from the 3DBMD recording device 5a (Step 202a). Next, the user inputs the processing command 203 by using the input device 2. The processing command 203 is a command for decomposing the primitive 3DBMD 102 or extracting a part of the primitive 3DBMD 102. In response to the processing command 203, the data processing device 3a applies image processing to the primitive 3DBMD 102 (Step 204), and then generates the latest 3DBMD 103 (Step 205). In case that the user inputs the display command 208 in this step, rendering processing is applied to the latest 3DBMD 103 in order to generate the three-dimensional bit map display image data 104, and then the three-dimensional bit map display image data 104 is transferred to the display device 4 and the latest 3DBMD 103 is displayed (Step 209). According to those procedural commands, the procedural operation history data 105 is generated by the data processing device 3a (Step 210). In addition the data processing device 3a generate the index data from the displayed image (Step 211). The procedural operation history data 105 and the index data 106 generated in the previous steps are stored in the index and procedural operation history attached 3DBMD recording device 5c in the format for the index and procedural operation history attached 3DBMD 114 together with the primitive 3DBMD 102. The procedural steps from the step 203 for accepting the procedural command to the step 211 are repeated for the continuous processing. The index data 106 and the procedural operation history data 105 are updated sequentially in the index and procedural operation history attached 3DBMD recording device 5c.

In case that the user inputs the index data review command 212 with the input device 2, the data processing device 3a displays a list of the stored index data 106 on the display device (Step 213).

Alternately, in case that the user inputs the index data selection command 214 for selecting one of the displayed index data 106, the selected index data 106 is extracted and its magnified view is displayed on the display device 4 (step 209).

Thus, along with the procedures for applying the image processing to the primitive 3DBMD and generating the latest 3DBMD 103, the procedural operation history data 105 and the index data 106 are stored sequentially.

The user inputs the save command 206 when he or she reaches the desired latest 3DBMD 103. The save command 206 specifies the data recording format. When storing the latest 3DBMD 103 currently processed, in case of storing the current procedural operation history data 105 and the index data 106 together with the primitive 3DBMD 102, the data storing in the format for the index and procedural operation history attached 3DBMD 114 is specified, and alternatively, in case of storing the current procedural operation history data 105, the index data 106 and the primitive 3DBMD 102 as well as the current latest 3DBMD 103, the data storing in the format for the primitive, index and procedural operation history attached 3DBMD 113 is specified.

If necessary, the user specifies the print-out operation for the required image at the printing means (not shown).

The procedural flow is completed after storing the data.

For the 3DBMD without its index data 106 generated after capturing the image, its index data 106 and procedural operation history data 105 can be generated by executing the procedural flow described above.

In case of storing the data in the format for the primitive, index and procedural operation history attached 3DBMD, the stored data can be supplied for the forthcoming operation allowed to start with the latest 3DBMD. As the stored data includes the primitive 3DBMD, by combining the primitive 3DBMD and the procedural operation history data, a series of past operations for generating the latest 3DBMD can be replayed and any state between the primitive 3DBMD and the latest 3DBMB can be recalled as the start point of the user's operation.

In addition, in case of storing the data in the format for the index and procedural operation history attached 3DBMD, as only the primitive 3DBMD, the index data and the procedural operation history data are recorded, the volume of the stored data can be reduced.

Figure 3:
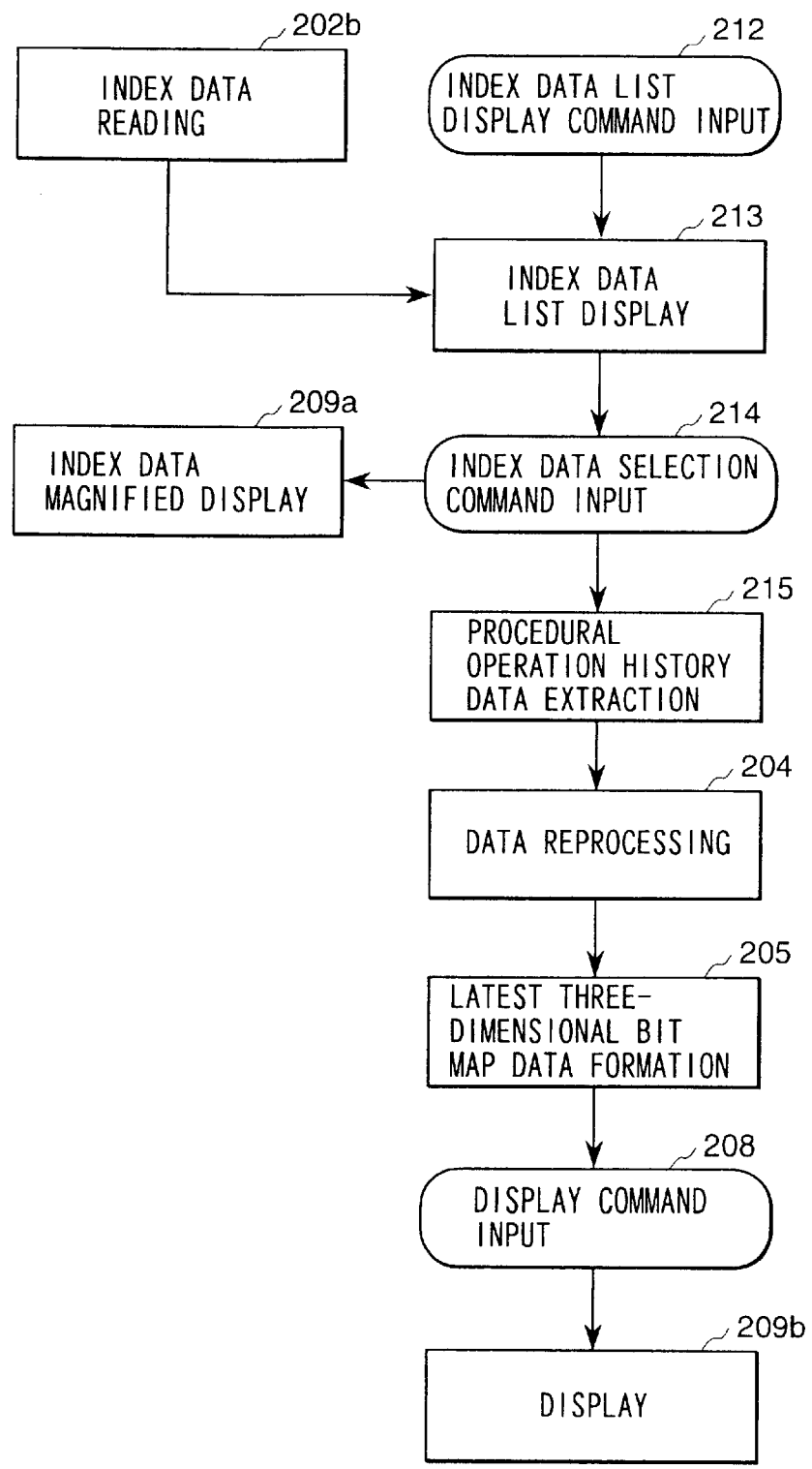
FIG. 3 is a reprocess flowchart.

Next, what is described is the procedural flow performed by the 3DBMD processing system 1a for displaying the desired 3DBMD promptly by using the index data 106 of the 3DBMD having the index data 106 and the procedural operation history data 105 (that is, the 3DBMD having a data format for the index and procedural operation history attached 3DBMD 114). This procedural flow is shown in FIG. 3.

At first, the user inputs the index data display command 212 by using the input device 2. In responsive this command, the data processing device 3a extracts and reads in the index data 106 from the index and procedural operation history attached 3DBMD recording device 5c (Step 202b), and displays a list of index data 106 on the display device 4 (Step 213).

Next, the user specifies one of the index data 106 corresponding to his or her necessary 3DBMD in the displayed list of index data 106, and inputs the index data selection command 214 from the input device 2. In response to the index data selection command 214, the data processing device 3a displays a magnified image of the selected index data 106 on the display device 4 (209a). Next, the data processing device 3a extracts the procedural operation history data 105 and the primitive 3DBMD 102 corresponding to the extracted index data 106 from the index and procedural operation history attached 3DBMD recording device 5c (step 215). The procedural operation history in the extracted procedural operation history data 105 is applied to the primitive 3DBMD 102 (Step 204). This data to which the procedural operation history corresponds to the latest 3DBMD 103 to be obtained when the extracted index data 106 was generated. The user inputs the display command 208 by using the input device 2, and the data processing device 3a display the rendered image of the latest 3DBMD 103 on the display device (Step 209b).

According to this embodiment, as the index data does not requires the rendering operation when displaying the index image, it will be appreciated that the data content can be reviewed in a shorter time of period than displaying the rendered image of the latest 3DBMD for the initial display operation. As plural sets of index data can be displayed all together, it will be appreciated that the time spent for display operation can be made shorter than generating plural rendered images of the latest 3DBMD and displaying them in a single screen. As plural index data are stored, it will be appreciated that plural sets of the latest 3DBMD can be generated from the procedural operation history data and the primitive 3DBMD. As the plural sets of the latest 3DBMD are generated on demand from the procedural operation history data and the primitive 3DBMD, it will be appreciated that the volume of the stored data can be reduced in comparison with the case in which the plural sets of the latest 3DBMD are stored corresponding to the plural sets of index data.

Figure 9:
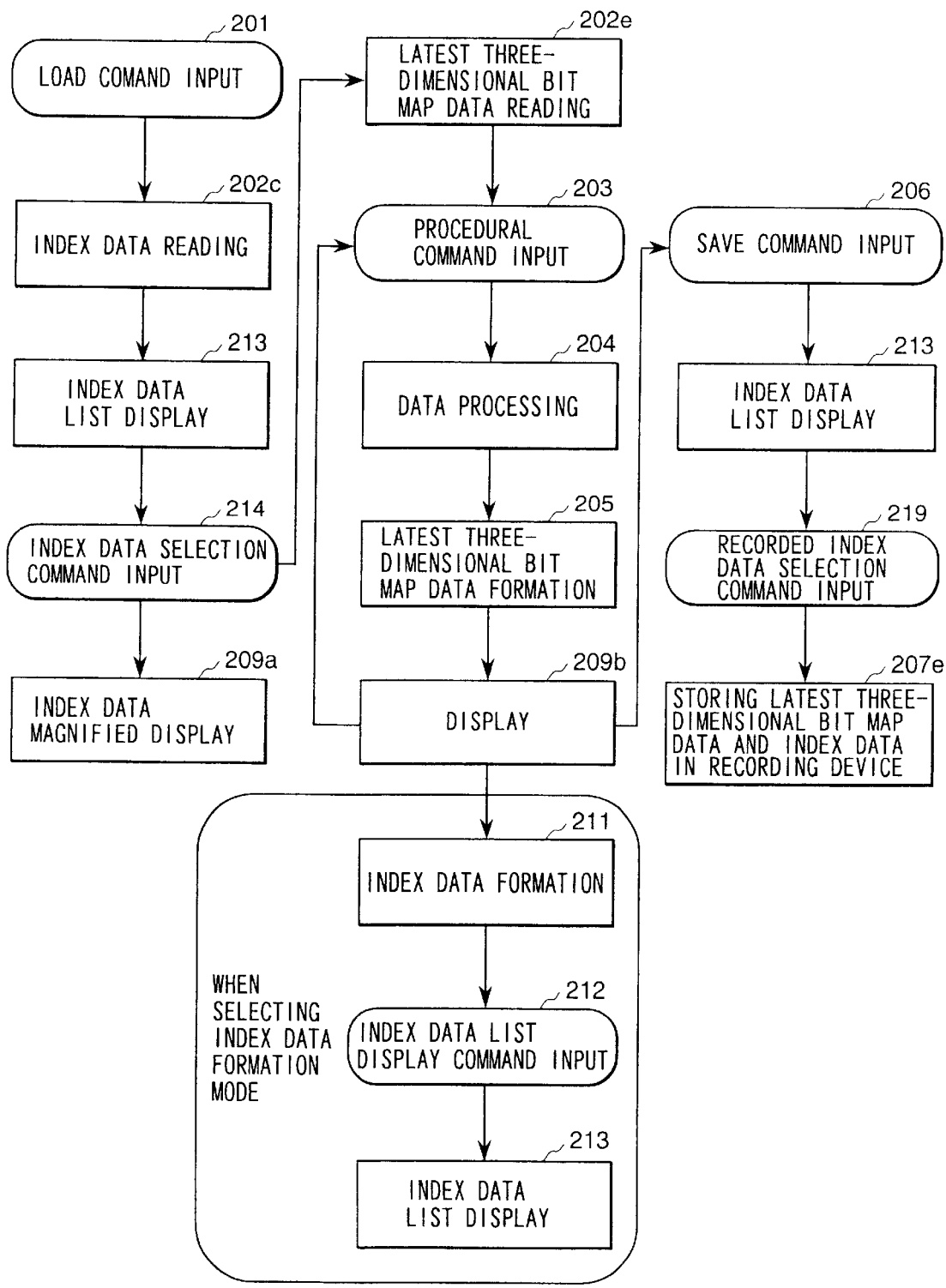
FIG. 9 is a process flowchart.

Next, the procedural flow performed by the 3DBMD processing system 1a for editing the 3DBMD having the index data is described. Its procedural flow is shown in FIG. 9. The data format used in this embodiment is a format for the primitive, index and procedural operation history attached 3DBMD. This procedure can be also applied to the data format for the index and procedural operation history attached 3DBMD.

At first, in response to the load command 201 input by the user, the processing system reads in the index data 106 from the primitive data and index attached 3DBMD recording device 5b (Step 202c), and displays their list (Step 213). Next, the user is required to input the index data selection command 214, and the index data 106 corresponding to the 3DBMD to be edited is selected. It is allowed to display a magnified view of the index data 106 (Step 209a). Next, the latest 3DBMD 103 corresponding to the selected index data 106 is read in from the primitive and procedural operation history attached 3DBMD recording device 5b (Step 202e). In case of editing the index and procedural operation history attached 3DBMD, the latest 3DBMD 103 is generated by selecting the index data 106 at first, and then applying the procedural history specified by the procedural operation history data 105 to the primitive 3DBMD. The subsequent editing procedures are the same as those shown in this embodiment.

Next, in response to the procedural command 203 input by the user, the data processing device 3a applies the image processing to the data (Step 204). In this case, the procedural commands 203 includes the operation for data extraction, view point rotation and display mode alteration for density data. And then, the data processing unit 3a generates the latest 3DBMD (Step 205) and displays it on the display device 4 (Step 209b). The user, viewing this display image, inputs the procedural command again for the further editing operation, and then the procedural flow from the procedural command input 203 to the display 209a are repeated. Every time when the display operation 209a is performed, the index data 106 is generated and stored in the recording unit. In case that the user may request to review the course of editing procedures, the user is prompted to input the index data list display command (Step 212), and then the index data list is displayed (Step 213). The recording procedure for the index data 106 under edition can be interrupted by the user setting.

Now that the user can obtain his or her desired latest 3DBMD 103 by repeating the editing procedures described above, the user is prompted to input the save command (206). In response to the user's input of the save command, the data contents initially loaded in the primitive data and procedural operation history attached 3DBMD recording device 5b are updated with the current procedural operation history data 105, the current index data 106 and the current latest 3DBMD. The data (the index attached latest 3DBMD 115) in the user's specified data format including the latest 3DBMD 103 and the index data 106 for the latest 3DBMD 103 is recorded in the index attached latest 3DBMD recording device 5d. In case of suspending the editing procedure, the data is not recorded into the index attached latest 3DBMD recording unit 5d.

Figure 10:
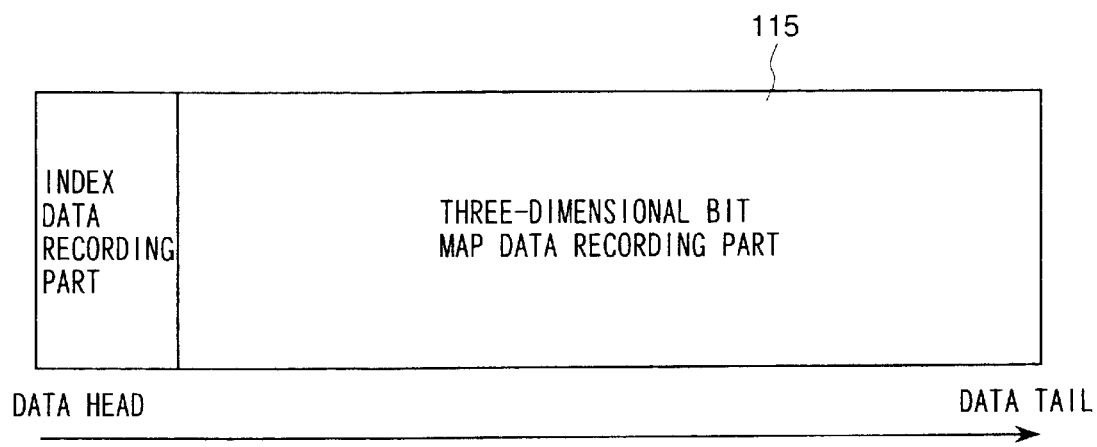
FIG. 10 is an example of three-dimensional bit map data format.

FIG. 10 shows a data format for the index attached latest 3DBMD 115. This format has a header for the index data recording part followed by the latest 3DBMD recording part. The index attached latest 3DBMD 115 has an index data part at its header in the data format for storing the data with its editing procedure completed, which allows to review the contents of the 3DBMD without reading directly the latest 3DBMD. This makes it possible for the user to retrieve promptly his or her desired data by viewing a list of index data even if the user has already stored numerous 3DBMD's. In addition, for the data potentially to be unused for the future editing operations, the overall volume of data can be reduced much more than the case in which the primitive 3DBMD's not possible to be used later are stored together.

After the editing operations, the user stores the index attached latest 3DBMD 115 and completes the editing operations.

What described above is a procedural flow in which the user edits the 3DBMD obtained by capturing the image of the object by X-ray CT and obtains his or her desired image.

Now, the display screen of the index data is described next.

Figure 6:
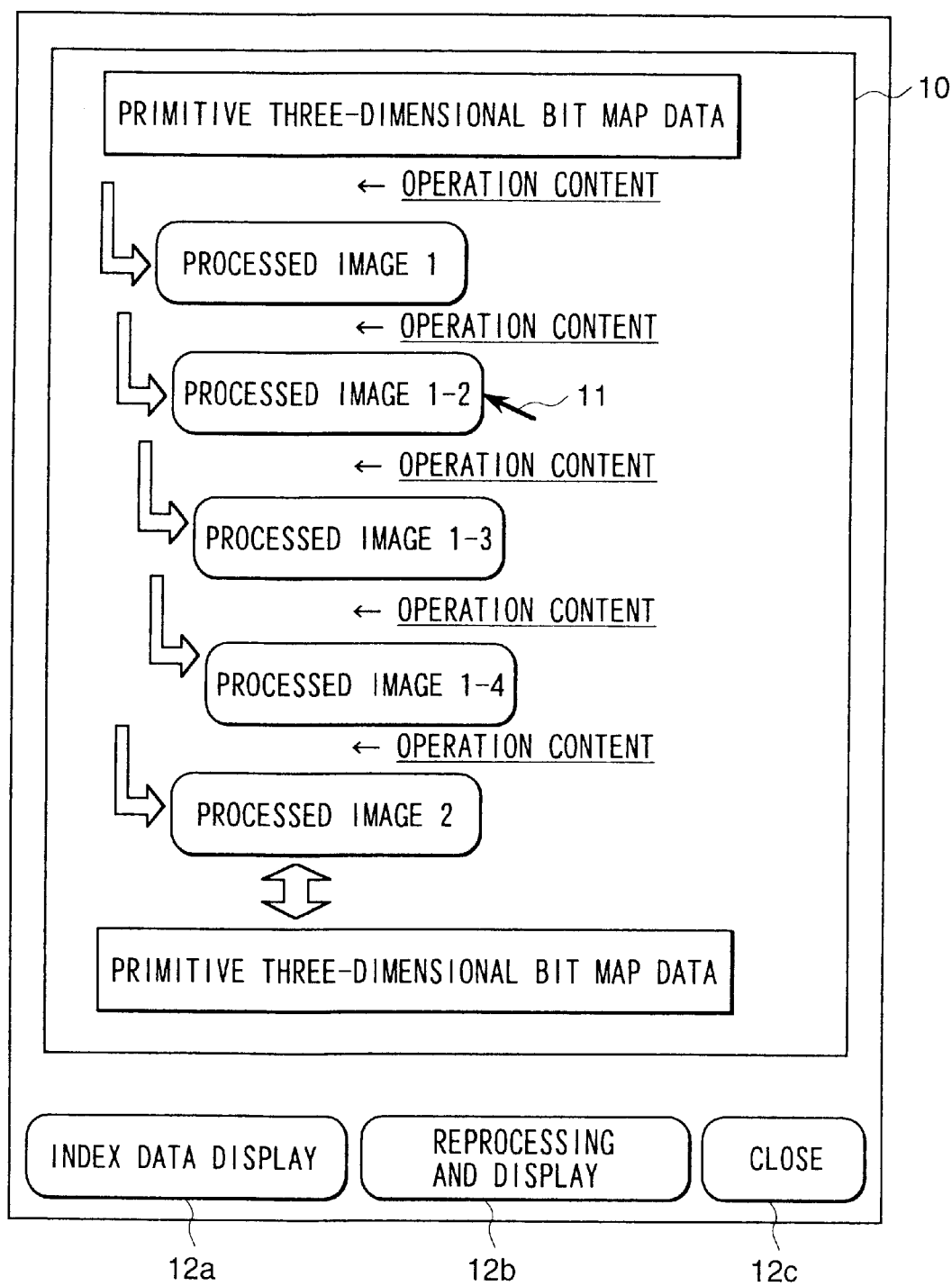
FIG. 6 is an example of index data display and selection screen.

FIG. 6 illustrates a history display screen in case that a list of the index data 106 is displayed in terms of its procedural operation history and operation content. The history display screen 10 presents hierarchically the individual step of operations and the individual part of decomposed images. The history display screen shows the contents of the operations at the individual steps for the primitive 3DBMD to the latest 3DBMD. Each of the contents is recorded as the index data 106. The use can select the operation displayed on the screen by using the pointer 11 with the mouse or the arrow keys of the keyboard. The detail of the operation content and the index data corresponding to the image after applying the designated operation can be displayed by specifying the operation step. The history display screen 10 includes the button 12a for directing the data display command, the button 12b for directing the reprocessing and display command, and the button 12c for closing the screen.

The user may select the operation step and press the reprocessing and display button. In response to this user's action, the data processing unit 3a applies the procedural operation history data 105 covering the procedures up to the selected operation to the primitive 3DBMD, and then displays the rendered image on the screen.

Figure 7:
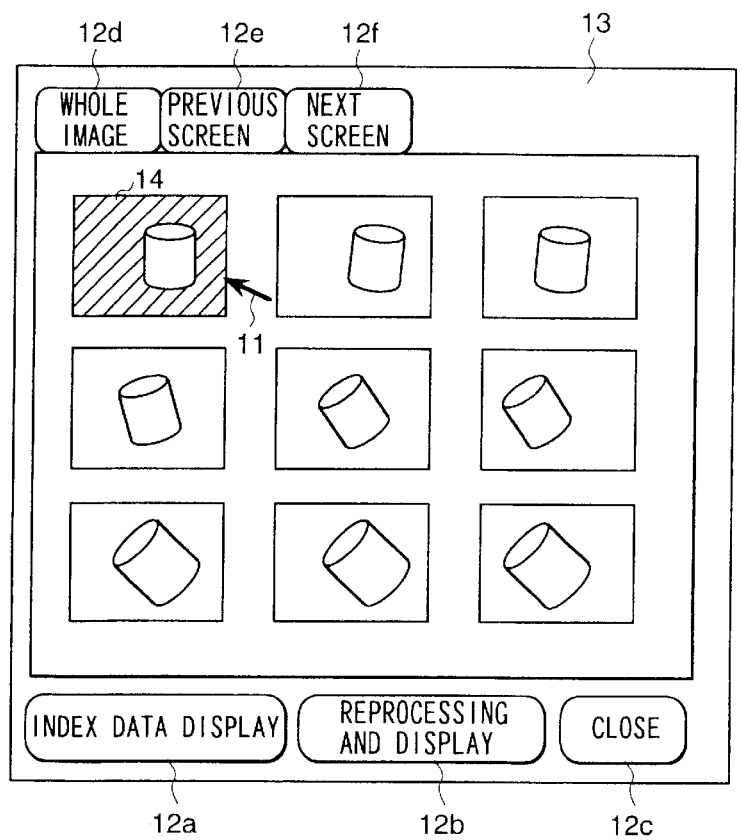
FIG. 7 is an example of index data display and selection screen.

FIG. 7 illustrates a list display screen 13 in case of displaying a list of index data 106 as images. The list display screen 13 displays the images retrieved as the index data obtained after applying the designated operations to the primitive 3DBMD to the latest 3BMD. The user can select the images on the screen by using the pointer 11 with the mouse or the arrow keys of the keyboard. The background color of the selected image 14 is made change so as to be distinguished from others, which makes the user recognize its selection status. The selected image 14 may contain the detail of the corresponding operation content, or its selected and magnified view may be displayed. The list display screen 13 includes the button 12a for directing the index data display command, the button 12b for directing the reprocessing and display command, and the button 12c for closing the screen. In case that the selected image can not displayed in a single screen, the user may use the button 12d for requesting to display its whole image in a reduced scale, and the previous-screen button 12e and the next-screen button 12f for scrolling the pages covering the whole image.

The user may select the operation step and press the reprocessing and display button. In response to this user's action, the data processing unit 3a applies the procedural operation history data 105 covering the procedures up to the selected operation to the primitive 3DBMD, and then displays the rendered image on the screen.

Figure 8:
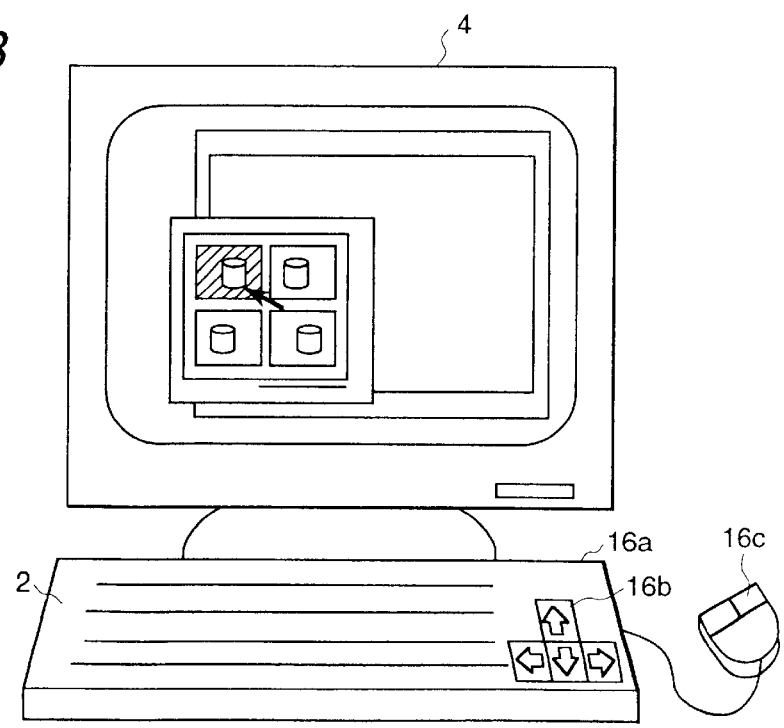
FIG. 8 is an example of user input and display device.

FIG. 8 illustrates the input device 2 and the display device 4. The display device 4 is connected to the input device 2, and the user viewing the display screen 4 operates the input device. The input device 2 is composed of the keyboard 16a, the arrow keys 16b and the mouse 16c. The keyboard 16a is used for accepting the numerical data input and the command input, the arrow keys 16b are used for specifying the image 14 selected in the images displayed on the screen and the mouse 16c is used for selecting the images and the operations along with the movement of the pointer 11.

According to the above described three-dimensional bit map data processing, by using the 3DBMD having the index data, the time spent for displaying the index data can be made shorter than the time spent for rendering the 3DBMD and displaying the rendered image, and thus the time spent for confirming the content of the 3DBMD can be reduced.

In addition, by storing the history of operations applied to the 3DBMD, a designated steps of operations can be replayed and an arbitrary state backward from the completed 3DBMD can be restored. This means that the undo operation can be applied to the completed 3DBMD.

By storing the 3DBMD before image operations, the 3DBMD after image operations, the procedural operation history data and the index data, the content of the data can be confirmed when restarting the operation. In addition, after confirming the content of the data, the operation for the completed 3DBMD can be restarted. In case of reprocessing the 3DBMD processed before the completed 3DBMD, by applying partially the operations recorded in the procedural operation history data to the completed 3DBMD, the 3DBMD traced backward from the completed 3DBMD can be generated. By applying the image operations to this traced-back 3DBMD, the steps experienced up to the completed 3DBMD can be reattempted.

In this embodiment, the data formats for the primitive, index and procedural operation history 3DBMD, the index and procedural operation history 3DBMD and the index attached latest 3DBMD define the sequence of the index data, the procedural operation history data, the primitive 3DBMD and the latest 3DBMD, which may not be required to be arranged physically and sequentially in the order specified by the data format on the surface of the recording media (for example, the surface of the hard disk in the hard disk recording device) but may be accessed logically in this specified order by the recording device. In addition, even if at least one part of the index data, the procedural operation history data, the primitive 3DBMD and the latest 3DBMD might be recorded physically in a separate recording device, it is allowed to access and readout the designated data logically in this specified order. And furthermore, it is allowed to read out the individual data separately and arrange them in a random access memory so that the data may be ready to be accessible in the random access memory on demand.

The data format for the index attached latest 3DBMD can be used for storing large volume CAD data. Though it is not required to applying the rendering processing to the CAD data for generating its display image, as the large volume CAD data requires an extended period of time for reading in the data and performing complicated topological calculations for generating images, it takes a long period of time to display the images as is the case with the latest 3DBMD. The images can be displayed rapidly by recording the index data at the header of the data contents. In this case, the data format of the index data does not require the topological calculations.

Figure 17:
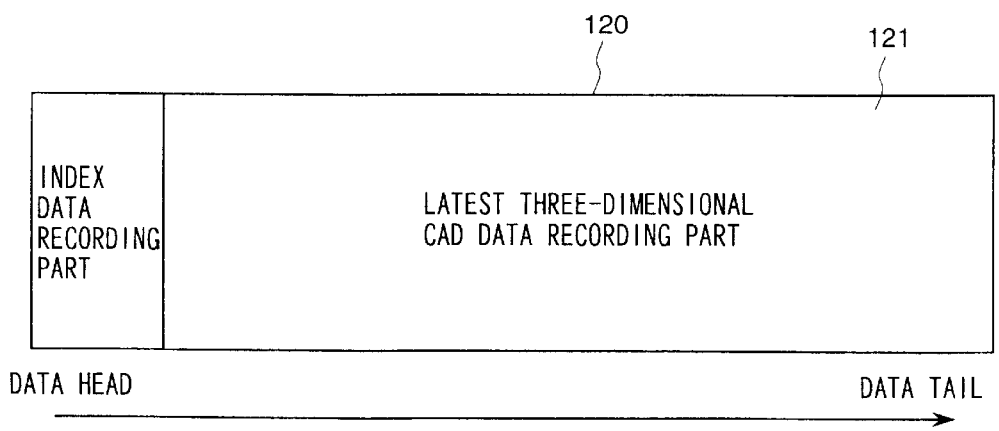
FIG. 17 is an example of CAD data format.

FIG. 17 shows the data format 120 for the index three-dimensional CAD data. The latest three-dimensional CAD data is recorded after the index data 122.

Embodiment 2

This embodiment uses a scale-down 3DBMD in stead of the index data 106 used in the embodiment 1.

At first the sample is scanned by the three-dimensional X-ray CT. The captured data is stored as the primitive 3DBMD in the memory device (a hard disk in this embodiment).

Next, the primitive 3DBMD is made converted into the 3DBMD in this embodiment. FIG. 13 shows an example of the 3DBMD data format having the scale-down 3DBMD in this embodiment.

Figure 13A:
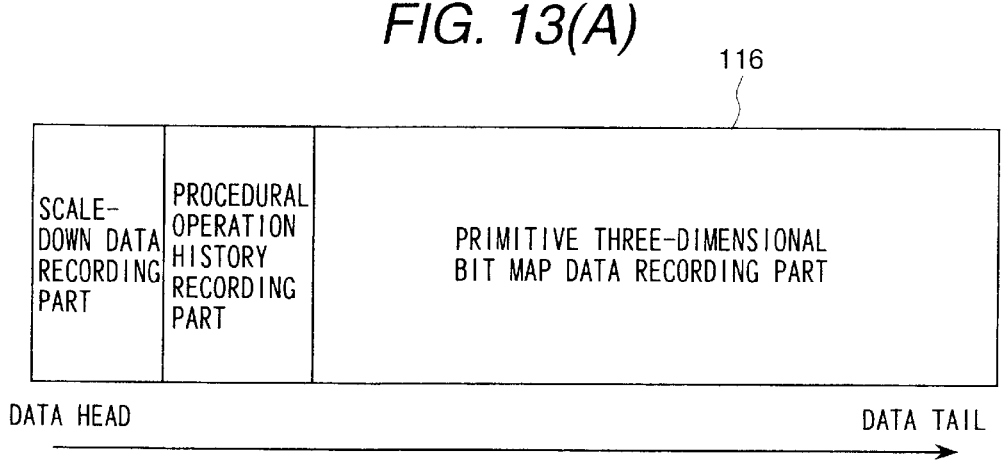
FIGS. 13(A)–13(C) are examples of three-dimensional bit map data formats.

The scale-down and procedural operation history attached 3DBMD 115 shown in FIG. 13(A) has a scale-down 3DBMD recording part at the data header followed by a procedural operation history data recording part, and the primitive 3DBMD recording part is recorded at the aftermost part. The scale-down 3DBMD is a reduced data of the 3DBMD obtained by applying the processing directed in the procedural operation history data to the primitive 3DBMD (namely the reduction of the latest 3DBMD). As the data volume of the scale-down 3DBMD is smaller than the data volume of the 3DBMD, the time spent for reproducing the final display image is short in case of applying the rendering process. Therefore, the time spent for confirming the outline of the latest 3DBMD can be made shorter. As the scale-down 3DBMD is based on the 3DBMD, the operations for rotating and cutting the object can be applied to the data. The time spent for those operations can be extremely shorter than the case in which the same operations are applied to the latest 3DBMD. Therefore, the operations by the users to be applied to the latest 3DBMD may be applied preliminarily to the scale-down 3DBMD and then the outline of the operations' result can be confirmed. Now that the outline of the operations' result is confirmed, the same operations already confirmed can be applied to the latest 3DBMD. In case of applying the image processing to the large amount of data (such as the latest 3DBMD and the primitive 3DBMD), every step of procedures in the overall processing requires a long period of time (which may require the user to wait for ten minutes and a few minutes, which leaves the user on such a halfway as he or she can not leave the seat for expecting the result but he or she have to wait patiently forgetting the result), and thus the user have to assume the response time. Therefore, if one step of the processing is held until its prior step of the processing is completed, the overall response time makes extremely long. On the contrary, by means that, after the individual results in the plural steps of the processing are confirmed with their scale-down 3DBMD, the image processing steps recorded in the procedural operation history data and the first-time image processing steps are applied altogether, the user can do other jobs while waiting for the completion of applying the image processing to the primitive 3DBMD. Thus, the processing for the large volume 3DBMD can be performed efficiently. As the 3DBMD before the latest 3DBMD can be generated by using the primitive 3DBMD and the procedural operation history data in the similar manner to the embodiment 1, undo operations can be enabled.

Figure 13B:
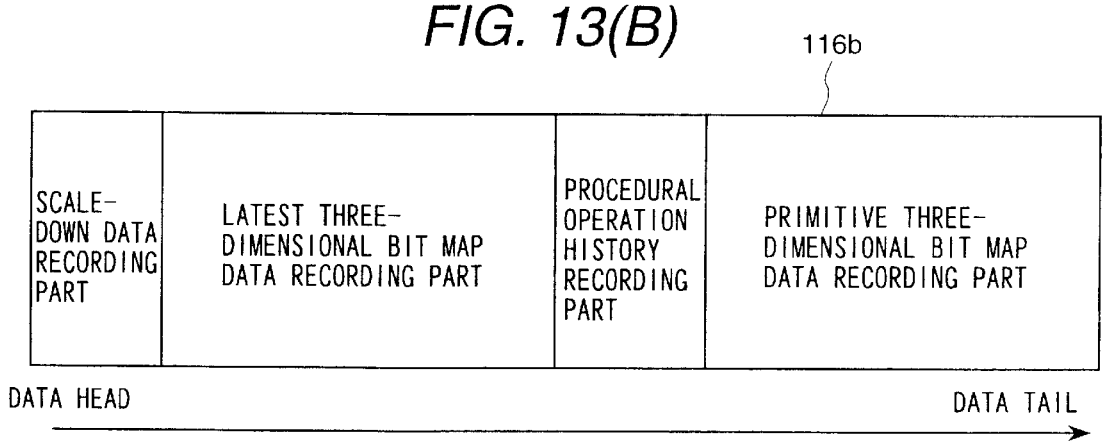

The primitive, scale-down and procedural operation history attached 3DBMD 115 shown in FIG. 13(B) has a data format for recording the primitive 3DBMD together when recording the processed latest 3DBMD. This data format has a scale-down 3DBMD recording part of the latest 3DBMD at the data header followed by the latest 3DBMD recording part, and a procedural operation history data recording part and a primitive 3DBMD recording part is recorded at the aftermost part. The scale-down 3DBMD is updated every time when the latest 3DBMD is modified. The procedural operation history data records the steps of the processing performed from the primitive 3DBMD to the latest 3DBMD. According to this data format, the user can confirm the outline of the latest 3DBMD by viewing the scale-down 3DBMD. In case of attempting to regenerate the latest 3DBMD (when undo the past processing applied to the latest 3DBMD), the desired 3DBMD to be obtained by applying the undo operation for the past processing can be generated equivalently by applying the procedural operation history data corresponding to the designated step to the series of past procedures to the primitive 3DBMD by referring to the primitive 3DBMD and the procedural operation history data. In addition, the operations by the users to be applied to the latest 3DBMD may be applied preliminarily to the scale-down 3DBMD and then the outline of the operations' result can be confirmed. Therefore, by means that, after the individual results in the plural steps of the processing are confirmed with their scale-down 3DBMD, the first-time image processing steps are applied altogether, the user can do other jobs while waiting for the completion of applying the image processing to the primitive 3DBMD. Thus, the processing for the large volume 3DBMD can be performed efficiently. As the latest 3DBMD is recorded, a faster processing can be performed rather than the case in which the latest 3DBMD is generated by using the primitive 3DBMD and the procedural operation history data and then the first-time processing is applied to the latest 3DBMD.

Figure 14:
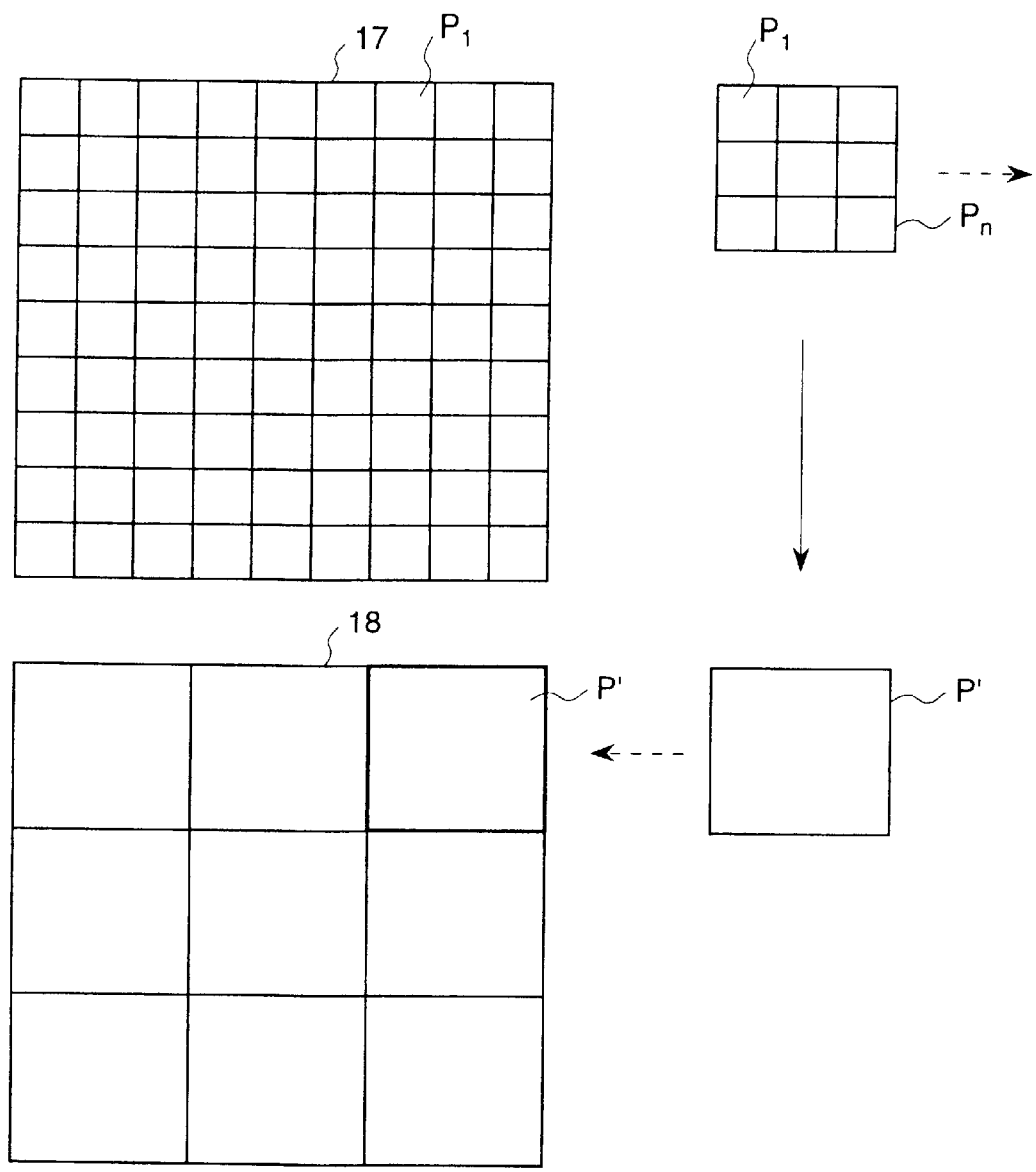
FIG. 14 is an example of generating scale-down bit map data.

By referring to FIG. 14, a method for generating the scale-down 3DBMD from the primitive 3DBMD (or the latest 3DBMD) is described below. For brief explanation, two-dimensional bit map data is used. This method can be applied equivalently to the 3DBMD in principle.

At first, the scale-down factor n is defined. Next, the primitive 3DBMD is loaded, and the size of the scale-down 3DBMD is determined by multiplying the size of the primitive 3DBMD and the inverse number of the scale-down factor n. Next, the pixel groups $P_1$ to $P_n$, each having $\sqrt{n} \times \sqrt{n}$ pixels, in the primitive 3DBMS are considered. Those pixel groups $P_1$ to $P_n$ are degenerated into a single pixel P', and the pixel value (color) V(P') of P' is calculated from the pixel value (color) of the individual pixels in the primitive 3DBMD as follows.

$$V(P')=V(P_1)+V(P_2)+ \ldots +V(P_n)/n$$

The above value is calculated for the individual pixel, and the scale-down 3DBMD 18 is generated. In this embodiment, this calculation is performed by the data processing device in response to the command directed by the user.

The large volume 3DBMD captured by the X-ray CT is converted into the scale-down 3DBMD by this method, and the scale-down 3DBMD is appended at the top of the large volume 3DBMD. At this step, the procedural operation history in the scale-down and procedural operation history attached 3DBMD 116 is initialized to be empty. Thereafter every time when the image processing are performed, the procedural operation history is added to the procedural operation history data. In case that the user prefers the data recording in the format for the primitive, scale-down and procedural operation history attached 3DBMD 116b, the data is recorded in the format for the primitive, scale-down and procedural operation history attached 3DBMD 116b by storing the scale-down and procedural operation history attached 3DBMD 115 with its data sequence reversed together with the processed 3DBMD.

Figure 11:
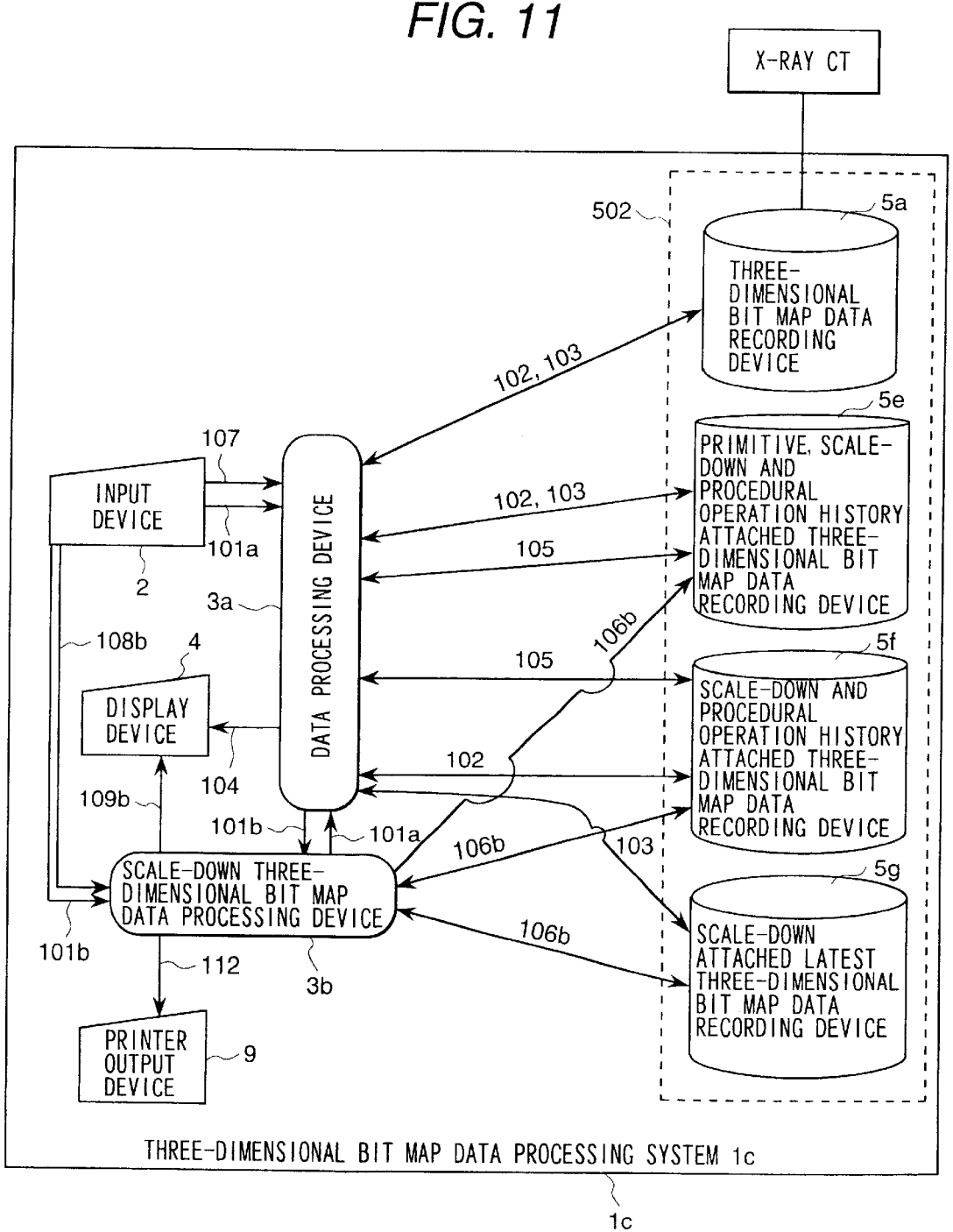
FIG. 11 is a system configuration diagram.

Next, FIG. 11 illustrates a schematic diagram of the structure of the 3DBMD processing system using two formats for the 3DBMD as described above. As the major parts of this system is the same as the embodiment 1, those like parts are not described below.

In this embodiment, the storage device 502 is so configured as to includes individually the 3DBMD recording device 5a, the primitive, scale-down and procedural operation history attached 3DBMD recording device 5e, the scale-down and procedural operation history attached 3DBMD recording device 5f and the scale-down attached latest 3DBMD recording device 5g, but the storage device 502 may be formed alternatively in another configuration as far as recording those elements of data. The electronic computer 503 is so configured as to include individually the data processing device 3a and the scale-down three-dimensional bit map processing device 3b, each corresponding to their specific tasks, which may be formed as a single computer performing those tasks.

The 3DBMD processing system 1c is a system which uses the scale-down 3DBMD instead of the index data 106 in the 3DBMD processing system 1a. The 3DBMD processing system 1c is formed by removing the index data display means 7a and the index data selection means 8 in the 3DBMD processing system 1a and adding the scale-down 3DBMD processing unit 3b for applying the image processing to the scale-down 3DBMD 106 in response to the scale-down 3DBMD processing command 101b. Its individual recording devices stores the scale-down 3DBMD instead of the index data. Those recording devices include the primitive, scale-down and procedural operation history attached 3DBMD recording device 5e for recording the primitive, scale-down and procedural operation history attached 3DBMD 116b, the scale-down and procedural operation history attached 3DBMD recording device 5f for recording the scale-down and procedural operation history attached 3DBMD 116, and the scale-down and latest 3DBMD recording device 5g for recording the scale-down and latest 3DBMD 116c.

Figure 12:
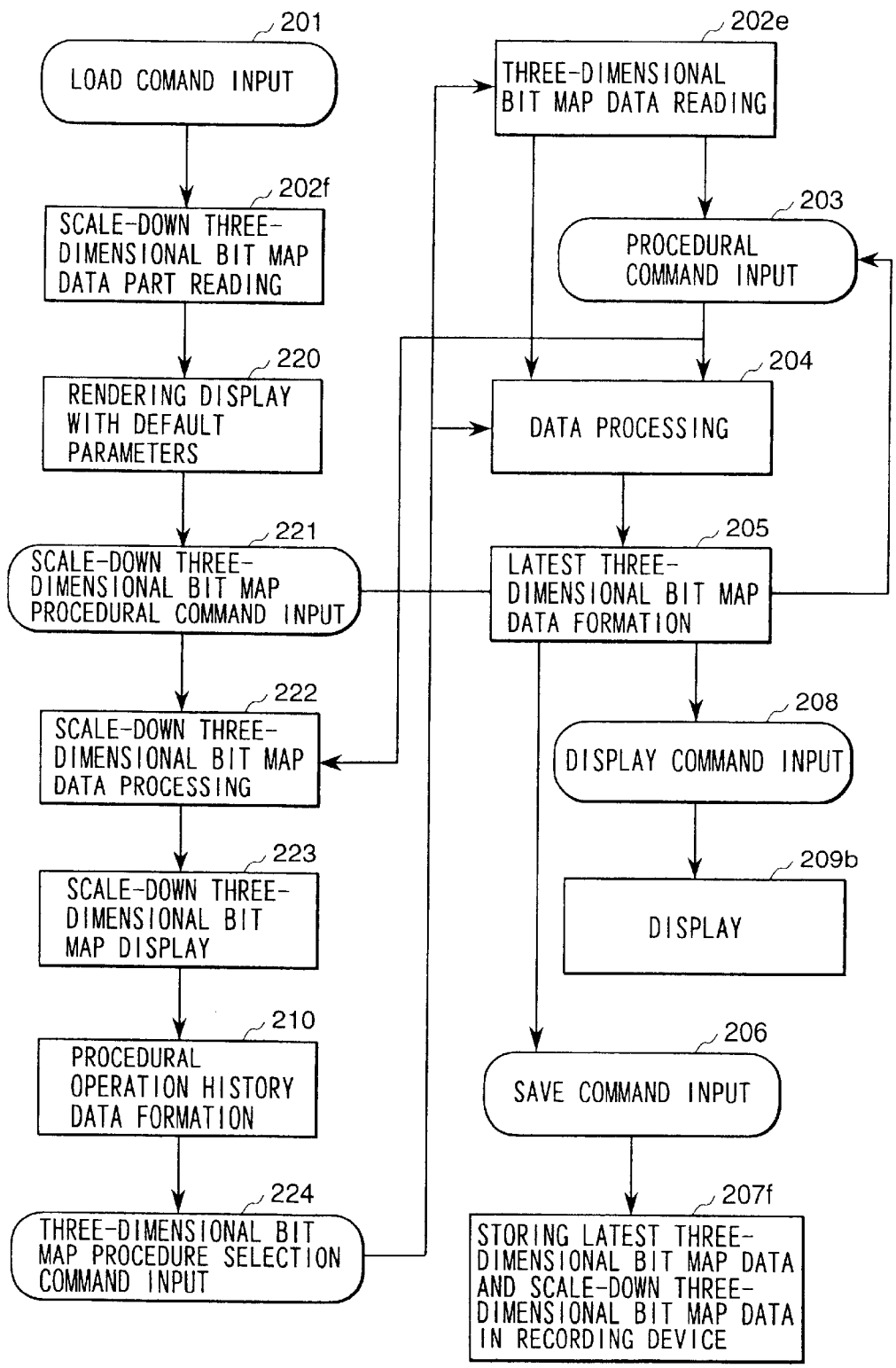
FIG. 12 is a process flowchart.

Next, the procedural flow performed by the 3DBMD processing system 1c for editing the 3DBMD having the scale-down down 3DBMD is described. Its procedural flow is shown in FIG. 12. The data format used in this embodiment is a format for the primitive, scale-down and procedural operation history attached 3DBMD. This procedure can be also applied to the data format for the scale-down and procedural operation history attached 3DBMD.

At first, in response to the load command 201 input by the user, the input device 2 sends the 3DBMD display command 108b to the scale-down 3DBMD processing device 3b. In response this display command, the scale-down 3DBMD processing device 3b reads the scale-down 3DBMD 106b from the primitive, scale-down and procedural operation history attached 3DBMD recording device 5e (Step 202f). The scale-down 3BMD processing unit 3b renders the scale-down 3DBMD 106 in accordance with the default parameters and then sends its result to the scale-down 3DBMD display image data 109b to the display device. The display device displays the scale-down 3DBMD display image data 109b (step 220). The default parameters are put into the system by the user prior to his or her work for specifying the display format and the visual angle when displaying the scale-down 3DBMD 106b for confirming the data contents, and if the user does not define those parameter values explicitly, the parameters preloaded at the system generation or installation are used.

Next, the scale-down 3DBMD 106 is processed. In response to the procedural command provided by the user, the input device 2 sends the scale-down 3DBMD processing command 101b to the scale-down 3DBMD processing device 3b (Step 221). In response to this command, the scale-down 3DBMD processing device 3b applies the image processing to the scale-down 3DBMD 106b (Step 222). This image processing includes rotation, decomposition and partial extraction operations.

Next, the scale-down 3DBMD processing device 3b generates the scale-down 3DBMD display image data 109b for the processed scaled-down 3DBMD 106b and transfers the data to the display device, and the display device displays the data (Step 223). The scale-down 3DBMD display image data 109b generates the procedural operation history data 105 and stores it in the memory (not shown) in the scale-down 3DBMD processing device 3b (or installed outside the scale-down 3DBMD processing device 3b).

As the scale-down 3DBMD is a small-size bit map data, the time spent for processing the scale-down 3DBMD is very short. This data has such a data format advantageous to the user by processing directly the scale-down 3DBMD as the time spent for processing the scale-down 3DBMD is very short while even though the result of the processing the large volume 3DBMD (including the primitive 3DBMD and the latest 3DBMD) can be confirmed briefly.

The user repeats the procedures from the step 221 through the step 210, and then identifies the procedural command providing a designated processing result.

The user, identifying the procedural command for his or her desired processing result (stored in the memory in the scale-down 3DBMD processing device 3b as the procedural operation history data 105), inputs the 3DBMD processing determination command (Step 224). In response to this command, the data processing device 3a reads in the latest 3DBMD 103 from the primitive, scale-down and procedural operation history attached 3DBMD recording device 5e (Step 202e). In case of using the scale-down and procedural operation history attached 3DBMD 116 as data, the same procedure as processed with the primitive, scale-down and procedural operation history attached 3DBMD 116b may be applied by generating the latest 3DBMD 103 from the primitive 3DBMD 102 and the procedural operation history data 105. The scale-down 3DBMD processing device 3b sends the procedural operation history data 105 stored in the memory to the data processing device 3a as the procedural command 101a.

Next, the data processing device 3a applies the procedural command 101a to the latest 3DBMD 103 (Step 204) and generates the latest 3DBMD 103 (Step 205). In case of executing plural procedural commands all at once, a given period of time is required. In this case, the user may leave the scene of his or her work and can be involved another job.

Now that the latest 3DBMD 103 is generated, the user inputs the display command 208. In response to the display command 208, the data processing device 3a renders the latest 3DBMD 103 and generates the 3DBMD display image data and sends it to the display device. The display device displays the 3DBMD display image data and the user confirms the displayed image.

The user, confirming the displayed image, determines whether further image processing is applied again to the scale-down 3DBMD 106b or any image processing is applied directly to the latest 3DBMD 103. In case of processing further the scale-down 3DBMD 106b, the procedural step goes back to the scale-down 3DBMD processing command input 221. In case of processing directly the latest 3DBMD 103, the procedural steps described in the next paragraph are applied. A direct processing of the latest 3DBMD 103 is used, for example, in case of modifying the resultant error between the latest 3DBMD and the processed scale-down 3DBMD 106b.

At first, the user inputs the procedural command 203. In response to this command, the input device sends the data processing command 101a to the data processing device 3a. The data processing device 3a sends the same procedural request to the scale-down 3DBMD processing device 3b as the scale-down 3DMD processing command 101b. The scale-down 3DBMD processing device 3b applies the scale-down 3DMD processing command 101b to the scale-down 3DBMD 106b, and then displays the scale-down 3DBMD 106b and generates the procedural operation history data 105. At the same time, the data processing device 3a applies the data processing command 101a to the latest 3DBMD 103 (Step 204). In this case, it should be noted that the time spent for processing the scale-down 3DBMD 106b is shorter than the time spent for processing the latest 3DBMD 103. Therefore, the user can review and study primarily the result obtained by processing the scale-down 3DBMD 106b.

Now that the user obtains his or her desired latest 3DBMD 103 at the end of the above procedures, the user inputs the save command 206. At the same time, the user selects the format to be used for storing the data. This format defines the scale-down and procedural operation history attached 3DBMD 115, the primitive, scale-down and procedural operation history attached 3DBMD 115b or the scale-down attached and latest 3DBMD 116c.

Figure 13C:
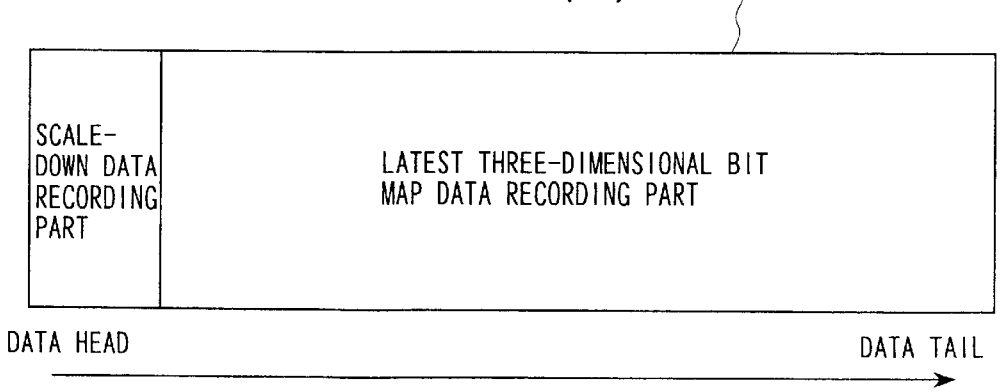

The format for the scale-down attached and latest 3DBMD 116c is described here. As shown in FIG. 13(c), the format for the scale-down attached and latest 3DBMD 116c has the scale-down 3DBMD at its header followed by the latest 3DBMD. The format for the scale-down attached and latest 3DBMD 115c is aimed for storing the data with its editing process completed, which allows the user to understand briefly the contents of the 3DBMD without reading the latest 3DBMD for viewing the data. Therefore, even in case that the user stores a number of 3DBMD, it will be appreciated that the user can retrieve his or her desired data rapidly by browsing a list of displayed scale-down 3DBMD. As the data size of the scale-down 3DBMD is small, the time spent for rendering, if any, might be very short. In addition, as the scale-down 3DBMD has a few possibility to be edited later, its data volume can be reduced much more than the case of recording its data together with the primitive 3DBMD not possible to be edited.

The latest 3DBMD is arranged in the format selected by the user and recorded in the recording device specific to the individual data format. The scale-down attached and latest 3DBMD 115c is recorded in the scale-down attached and latest 3DBMD recording device 5g.

At the end of the above editing procedures, the use stores the data and completes his or her editing work.

Figure 15:
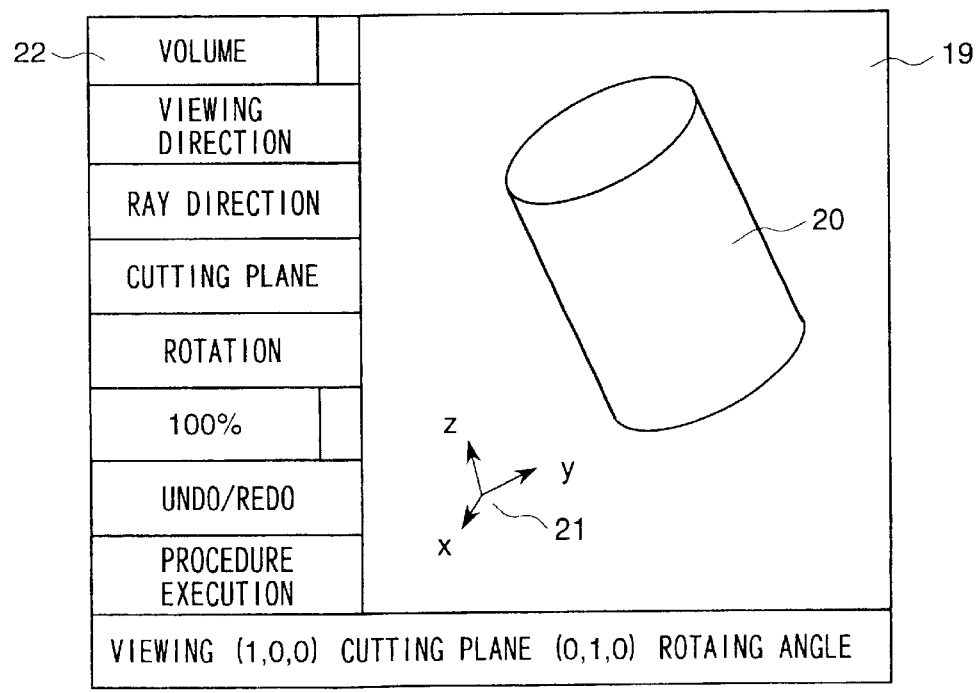
FIG. 15 is an example of scale-down bit map data display and process screen.

What described above is a procedural flow for editing the 3DBMD obtained by capturing the image of the object with X-ray CT in order to provide the output data in the format specified by the user. Next, the display screen for the scale-down 3DBMD is described. The component 24 [FIG. 15] shows a data processing and display screen for the scale-down 3DBMD in this embodiment. The scale-down 3DBMD processing and display screen 19 includes the rendered image 20 of the scale-down 3DBMD, the orientation indicator 21 allowing the user to recognize visually his or her sight direction, and the command selection panel 22, and the user can operates the scale-down 3DBMD by using the mouse, the keyboard and its arrow keys.

Figure 16:
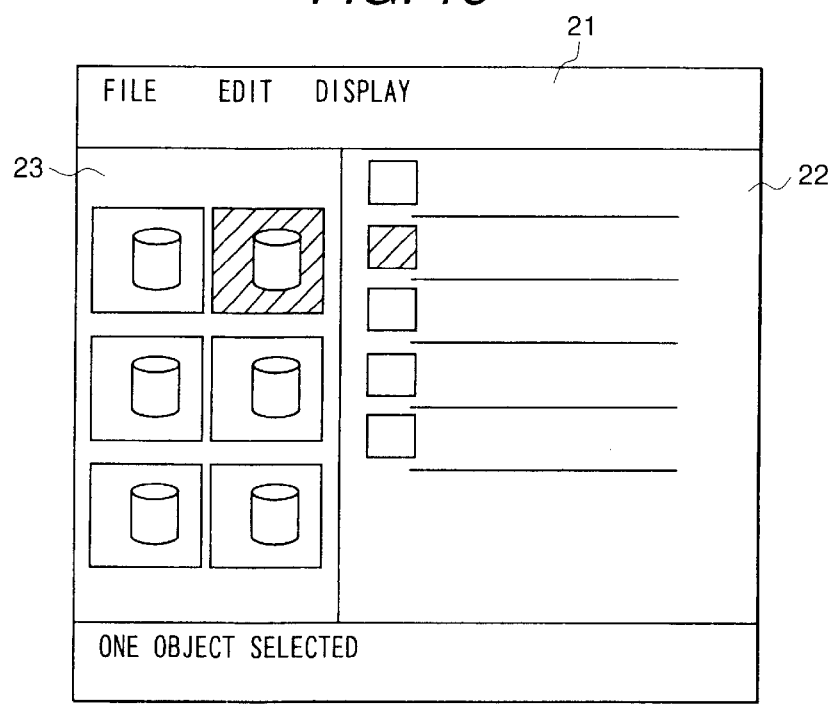
FIG. 16 is an example of operating system file display screen.

FIG. 16 shows a file manager screen. FIG. 16 shows a file manager screen including the area for displaying the outline of the data and the area for displaying a list of file names. A window area 23 is shown at the left side of the screen and shows the image obtained by rendering the scale-down 3DBMD. The window area 22 is also shown for displaying a list of file names. The windows area 23 presents rendered images of the scale-down 3DBMD 106b with their file names specified by the user using a mouse on the window area 22. The user can perform his or her operations in every window area by using a mouse, a keyboard and its arrow keys.

According to this embodiment, the same effect as brought by the embodiment 1 can be attained. In addition, by processing the data having the scale-down 3DBMD, the same process can be applied to the scale-down 3DBMD before processing the latest 3DBMD. As the time spent for processing the scale-down 3DBMD is shorter than the time spent for processing the latest 3DBMD, the outline of the processing result can be confirmed in a shorter period of time than the case of applying the processing directly to the latest 3DBMD.

Embodiment 3

Figure 18:
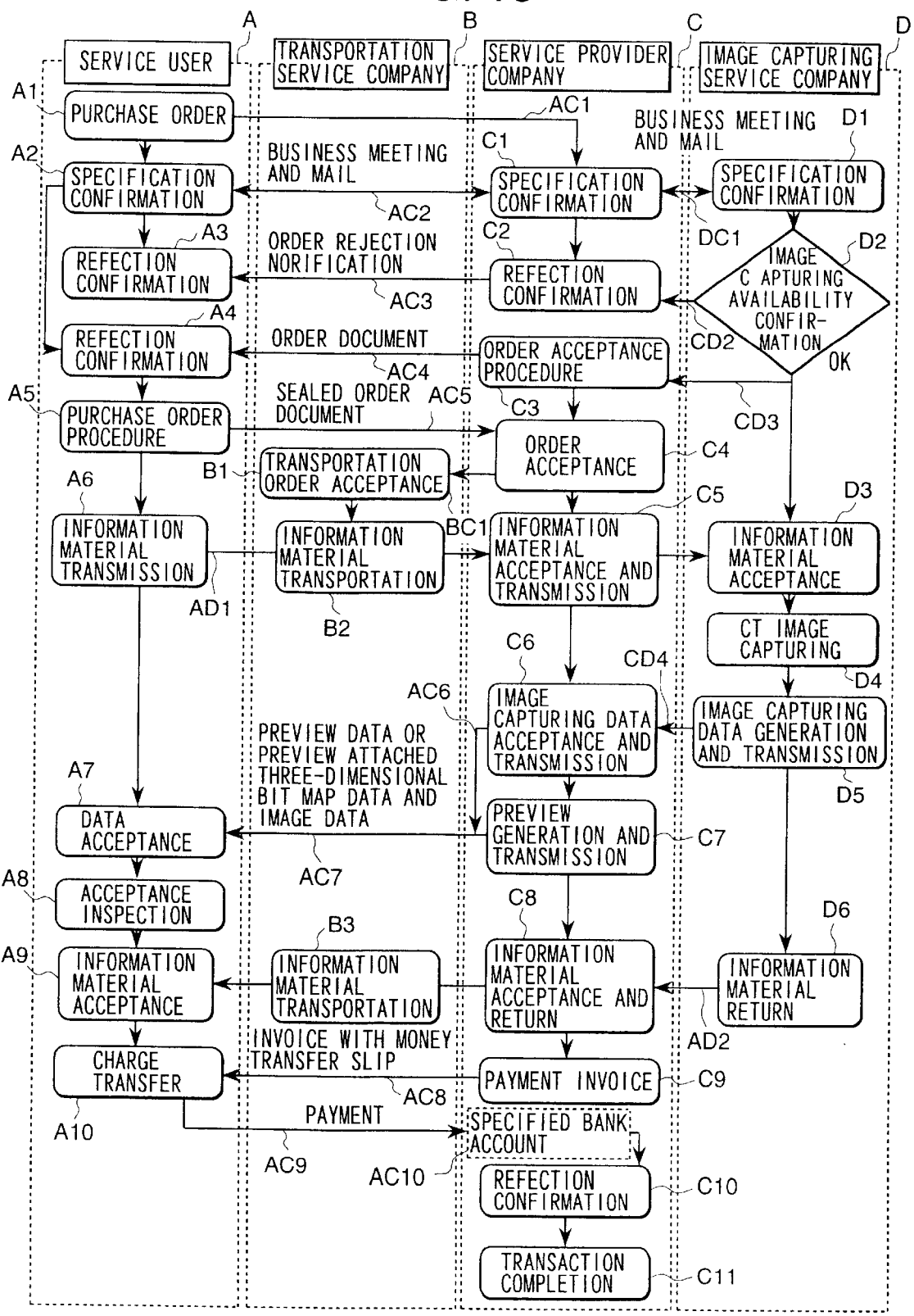
FIG. 18 is a business flow diagram.

Next, a business for providing the 3DBMD by using the 3DBMD described in the embodiments 1 and 2 is described. FIG. 18 shows a procedural flow of the 3DBMD provider service. In this embodiment, the following parties are concerned to one another; a service user A receiving the 3DBMD (generally, a corporate user), a service provider company C providing the 3DBMD, a transportation service company B delivering the target object from the service user A to the service provider company C, and an image capturing service company D (generally, operated by the service provider company C as its subsidiary business) capturing the image of the target object by using the X-ray CT apparatus. Their business flow is described below.

The service user A commits the service purchase order A1, and after transferring the order AC1 to the service provider company C, the service user A completes the specification confirmation A2 by exchanging information at the business meeting or mails AC2 (a mail means either of an e-mail or a postal mail) with the service provider company C. The service provider company C completes the specification confirmations C1 and D1 by exchanging information at the business meeting or mails CD1 about the specification AC1 with the image capturing service company D. After completing the specification confirmation D1, the image capturing service company D judges (at D2) whether the image capturing with the confirmed specification is possible or not, and if the image capturing will not be scheduled, the image capturing rejection notification CD2 is sent to the service provider company C. The service provider company C, receiving the image capturing rejection notification CD2, sends the order rejection notification AC3 to the service user A, and the overall flow is completed when the service user A confirms (A3) the order rejection notification AC3.

In case that the image capturing service company D sends the image capturing acceptance notification CD3 to the service provider company C, the service provider company C commits the order acceptance procedure C3, and sends the order document AC4 to the service user A. In this case, the order acceptance procedure C3 is a procedure for notifying the service provider A the fact that the purchase order is acceptable.

After confirming (A4) the order document AC4, the service user A commits the purchase order procedure A5. The service user fills out the order document at the purchase order procedure A5. Next, the service user A returns the order document to the service provider company C (AC5). The service provider company C, receiving the order document, commits the order acceptance and the image capturing arrangement C4. At this point, the service provider company C commits the request BC1 to the transportation service company B for picking up the target object at the service user A.

After completing the reception B1, the transportation service company B transports the target object from the service user A (AD1 and B2) to the service provider company B. The service provider company C receives the target object, and then transfer the target object to the image capturing service company D (C5). The image capturing service company D receives the target object (D3), and commits the CT image capturing D4 in accordance with the specification. The captured image data is generated by the image capturing (D5), and the captured image data is sent to the service provider company C (D5, CD4). The service provider company C receives the captured image data (C6), and generates (C7) the preview data (the index data 106 or the scale-down 3DBMD 106b) with the method shown in the embodiment 1 or 2. The preview data attached 3DBMD and the captured image data are sent to the service user A (AC7). The service user A receives the data (A7) and commits the acceptance inspection (A8).

At this point, the data volume of the captured image data, the latest 3DBMD and the primitive 3DBMD is very large. Therefore, instead of transferring the preview data attached 3DBMD and the captured image data to the service user A, only the preview data may be sent to the service user A first of all. As the service user A can understand the outline of the latest 3DBMD from the preview data, if further editions to be applied to the latest 3DBMD are required, the service user A sends his or her request to the service provider company and then the service provider sends the latest 3DBMD with necessary editions applied to the service user A.

If the preview data is the scale-down 3DBMD 106b, the service user A can recognize the necessary processes to be applied to the primitive 3DBMD by processing the scale-down 3DBMD 106b. The service user A sends its processing contents to the service provider C, and the service provider C applies this processing to the primitive 3DBMD 102. Finally, the service provider sends its result as the preview data attached 3DBMD to the service user A.

According to the above procedures, the volume of the data to be sent from the volume of data sent from the service provider to the service user after capturing the image can be reduced. Owing to this, it will be appreciated that the service provider can provide the service user with his or her desired data more rapidly than the first transmission of the captured image data. In addition, it will be appreciated that the service provider commits the processing to the large volume of 3DBMD all at once. Therefore, even in case that the service user does not have a system for processing the large volume of 3DBMD, the service user can get the resultant data obtained by processing the large volume of 3DBMD.

The image capturing service company D returns the target object to the service provider company C after completing the image capturing (D6). The service provider company C carries the target object back to the service user through the transportation service company B (C8, B3). The service provider company C, completing the shipment of the target object to the service user A, sends the invoice with money transfer slip for the payment invoice C9 to the service user A (AC8).

The service user A, receiving the captured image data (A7) and receiving the returned target object (A9), receives the invoice with money transfer slip and then commits the charge transfer A10 to the specified bank account AC10 (C11).

Embodiment 4

Figure 19:
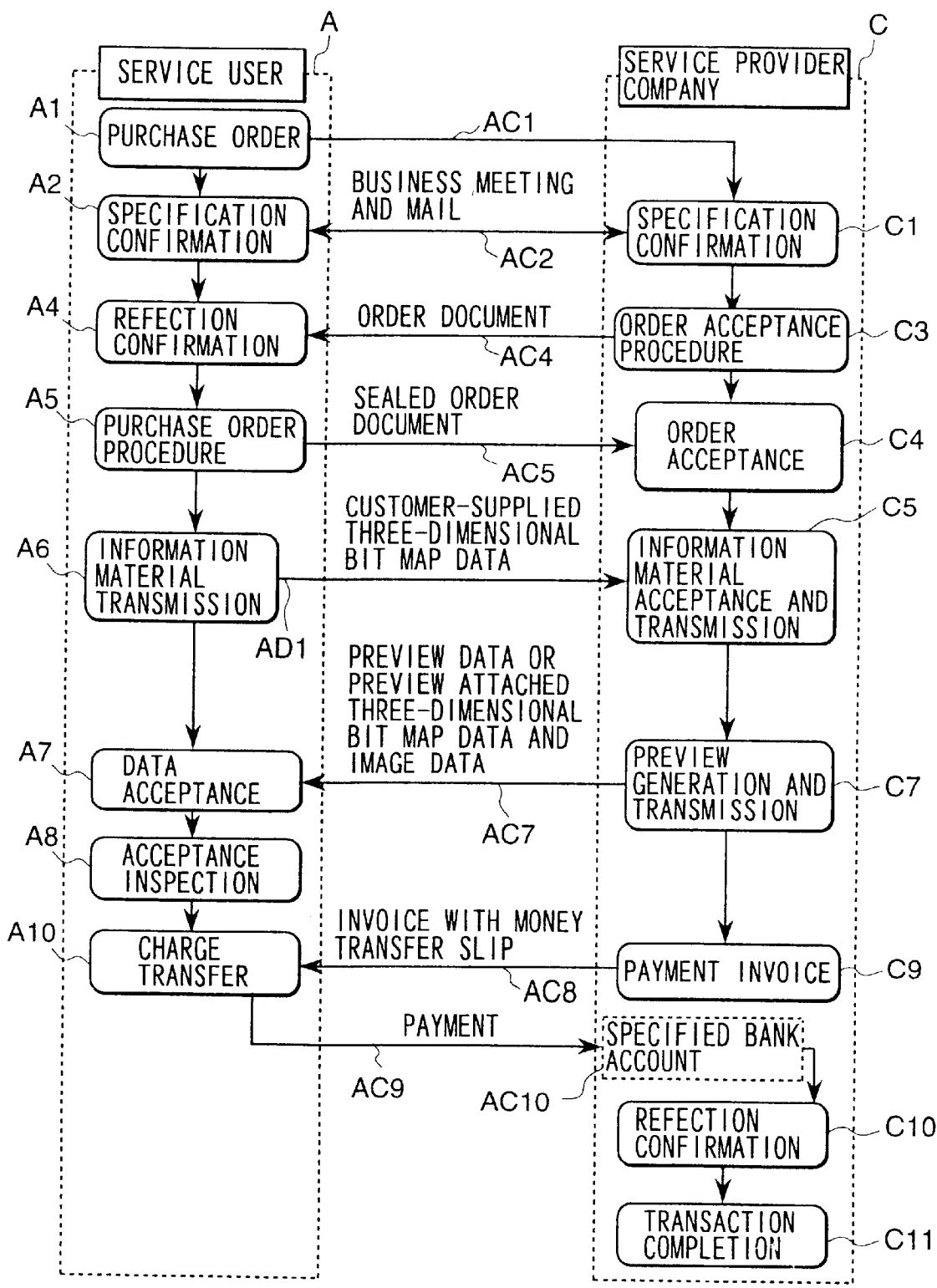
FIG. 19 is a business flow diagram.

Next, a business for providing the process for the 3DBMD by using the 3DBMD described in the embodiments 1 and 2 is described. FIG. 19 shows a procedural flow of the 3DBMD provider service in this embodiment. What will be described are the individual business flows by the service user A (generally, a corporate user) holding the original data of the 3DBMD and asking its image processing and the service provider company C providing the image processing to the 3DBMD.

The service user A commits the service purchase order A1. After transferring this.order AC1 to the service provider company C, the service user completes the specification confirmation A2 by exchanging information at the business meeting or mails AC2 with the service provider company C. The service provider company, receiving the order document AC4, identifies the order (A4) and commits the purchase order (A5). Then, the order document AC5 is returned to the service provider company C, and at the same time, the original data (3DBMD)AC11 is forwarded (A6). Receiving the preview data or the preview attached 3DBMD AC7 (A7), the service user commits the acceptance inspection A8 and transfers the payment AC9 to the specified bank account AC10 in response to the invoice with money transfer slip AC8 from the service provider company C, and finally all the transactions are completed.

Next, a business flow by the service provider company C is described. The service provider, receiving the order AC1 from the service user A, commits the order confirmation (C1) by exchanging information at the business meeting or mails (AC), and then commits the order acceptance procedure C3. The service provider company sends the order document AC4 to the service user A, and commits the order acceptance C4 in responsive to the returned order document AC5. The service provider company, receiving the original data (3DBMD) from the service user A, makes the preview data (index data 106 or scale-down 3DBMD 106b) of this original data by respecting the specification requirement by the service user A. Next, the preview data or the preview-attached 3DBMD AC7 is retuned to the service user A (C7). As in the embodiment 3, it is allowed to send the preview data to the service user at first and next send the large volume of 3DBMD to the service user after the service user identifies the result of the processing to be applied to the original data. The service user A can predict the result of the processing applied to the original data to some extent, but he or she can not confirms its result completely. In case that the service user A, receiving the preview data, recognizes it to be different from his or her expectation, by means that the service provider C attempts to apply alternative processing to the original data until the desired result can be obtained as in this embodiment, the data volume to be exchanged between the service user A and the service provider can be reduced much more than the large volume of 3DBMD is exchanged directly between them.

After the service user A confirms the contents of the processed data, the service provider sends the invoice with money transfer slip AC8 and commits the payment invoice C9. Finally, the service provider confirms (C10) that the service user A transfers the payment AC9 to the specified bank account AC10, and then completes the transaction.

According to the above embodiment, in dealing large amount of three-dimensional bit map data such as the primitive 3DBMD and the latest 3DBMD, it will be appreciated that the time spent for processing large amount of bit map data can be reduced by adding the data allowing the service user to identify easily the result of the processing to be applied to the original data.

What is claimed is:

1. A data processing method comprising:

a step of applying a plurality of processes for three-dimensional bit map data, recording information relating to a history of said processes, and rendering respective three-dimensional bit map data after said plurality of processes to generate a plurality of two-dimensional image data; and a step of displaying a list of said plurality of two-dimensional image data and processing said three-dimensional bit map data based on information relating to said history of said processes of said three-dimensional bit map data corresponding to two-dimensional image data selected in said list.

2. A data processing method of claim 1, wherein said three-dimensional bit map data is captured by X-ray CT.

3. A data processing method comprising a step for accepting an order for capturing an image by X-ray CT from a client;

a step for receiving an image—capturing target object from said client;

a step for forming a three-dimensional bit data by capturing said target object by said X-ray CT according to client's request;

a step for forming at least either of a scale-down three-dimensional bit map data generated by scaling down said three-dimensional bit map data or a two-dimensional bit map data generated by rendering and scaling down or rendering said three-dimensional bit map data;

a step for sending at least either of said formed scale-down three-dimensional bit map data or said formed two-dimensional bit map data; and a step for sending said three-dimensional bit map data to said client after establishing client's confirmation of said sent data.

4. A data processing method comprising a step for asking a service provider to capture an image of a sample by X-ray CT;

a step for sending said sample to said service provider;

a step for receiving at least one of data formed by said service provider, said data including a scale-down three-dimensional bit map data obtained by scaling down a three-dimensional bit map data captured by said service provider, a first index data obtained by rendering said three-dimensional bit map data and a second index data obtained by rendering and further scaling down said three-dimensional bit map data;

a step for confirming an image capturing result based on a content of data;

a step for replying said confirmation result to said service provider;

a step for accepting said three-dimensional bit map data from said service provider if said confirmation result is affirmative; and a step for requesting said service provider to recapture or reprocess said three-dimensional bit map data if said confirmation result is negative.

* * * * *